(12) United States Patent
Lassner et al.

(10) Patent No.: US 6,476,294 B1
(45) Date of Patent: *Nov. 5, 2002

(54) PLANT PHOSPHATIDIC ACID PHOSPHATASES

(75) Inventors: Michael W. Lassner, Davis; Diane M. Ruezinsky, Woodland, both of CA (US)

(73) Assignee: Calgene LLC, Davis, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/122,315

(22) Filed: Jul. 24, 1998

(51) Int. Cl.$^7$ .......................... A01H 5/00; C12N 15/82; C12N 5/04; C07H 21/04
(52) U.S. Cl. ................. 800/281; 800/298; 435/419; 435/468; 536/23.6
(58) Field of Search ................. 800/281, 298; 536/23.6; 435/69.1, 468, 419, 430

(56) References Cited

PUBLICATIONS van de Loo et al. PNAS, USA 92:6743–6747, Jul. 1995.*
De Luca, AgBiotech News and Information 5 (6): 225N–229N, Jul. 1995.*
Stymne, et al., "Triacylglycerol Biosynthesis" *The Biochemistry of Plants* vol. 9 pp: 175–214 (1987).
Kai, et al., "Cloning and Characterization of Two human Isozymes of Mg2+–independent Phosphatidic Acid Phosphatase", *The Journal of Biological Chemistry* (*1997*) vol. 272, No. 39 pp: 24572–24578.
Kai, et al., "Identification and cDNA Cloning of 335–kDa Phosphatidic Acid Phosphatase (Type 2) Bound to Plasma Membranes" *The Journal of Biological Chemistry* (*1996*) vol. 271, No. 31, pp: 18931–18938.
Kanoh, et al., "Phosphatidic acid phosphatase from mammalian tissues: discovery of channel–like proteins with unexpected functions" *Biochimica et Biophysica Acta* (1997) pp: 56–62.
Katagiri, et al., Abstract: "A Role of Phosphatidic Acid Phosphatase (PAP) in Cell Elongation in *Arabidopsis thaliana*", Plant and Cell Physiology (1998) 39 Suppl. pp. S124.
Sun, et al., "Acyl Coenzyme A Preference of the Glycerol Phosphate Pathway in the Microsomes from the Maturing Seeds of Palm, Maize, and Rapeseed" *Plant Physiol.* (*1988*) pp: 56–60.
Lohden, et al., "Triacylglycerol biosynthesis in developing seeds of *Tropaeolum majus* L. and *Limnanthes douglasii* R. Br." Planta (1992) 188:215–224.
Berg, et al., "Purification of a phosphatase which hydrolyzes phosphatidic acid, a key intermediate in glucolipid synthesis in *acholeplasma laidlawii* A membranes" *Biochimica et Biophysica Acta 1330* (*1997*) pp: 225–232.
Carman, George M., "Phosphatidate phosphatases and diacylglycerol pyrophosphate phosphatases in *Saccharomyces cerevisiae and Escherichia coli* " *Biochimica et Biophysica Acta* 1348 (1997) 45–55.
Katagiri, et al., Molecular cloning of a cDNA encoding diacylglycerol kinase (DGK) in *Arabidopsis thaliana* Plant Molecular Biology 30: 647–653 (1996).

* cited by examiner

Primary Examiner—Elizabeth F. McElwain
(74) Attorney, Agent, or Firm—Arnold & Porter

(57) ABSTRACT

By this invention, novel nucleic acid sequences encoding for phosphatidic acid phosphatase (PAP) proteins are provided, wherein said PAP protein is active in the formation of diacylglycerol from phosphatidic acid. Also considered are amino acid and nucleic acid sequences obtainable from PAP nucleic acid sequences and the use of such sequences to provide transgenic host cells capable of producing altered lipid compositions and total lipid levels.

24 Claims, 10 Drawing Sheets

FIG. 1b

```
CAAAAAACTTTATCTTTCCTTCCTTTGAAATCTCCCGGAGAAAAACTATAGAGATTTTCC
GTTTCCCGCTTTAATACAGTGCCCCAATTCGCGCGACACATAGAGTGTAGAGACGCTTTC
ACGAGCGTTTCCGACGTCGGACTTTCAGCTCATCATCTCCACATCTTTAACGGTAAAGAT
TAATCATGCCTGAAATTCATTTGGGTGCTCATACAATAAGATCCCATGGAGTAACAGTCG
CGAGGTTCCACATGCATGACTGGCTCATTCTTCTGCTGCTAATAGTCATTGAAATTGTTC
TTAATGTCATCGAACCCTTTCATCGTTTGTTGGAGAAGATATGCTCACTGATCTCAGAT
ACCCTCTGCAGGACAACACAATTCCTTTCTGGGCTGTCCCGTTGATAGCTGTTGTGCTAC
CTTTTGCTGTCATTTGTGTTTACTACTTCATTAGAAATGATGTTTATGACCTGCATCATG
CAATACTAGGGCTTTTGTTCTCTGTACTTATAACCGGTGTCATAACCGATGCTATAAAGG
ACGCTGTTGGTCGACCTCGTCCTGATTTCTTTTGGCGTTGTTTCCCTGACGGTATAGGGA
TCTTTCACAATGTCACGAAGAATGTTCTATGTACTGGAGCTAAGGATGTGGTCAAAGAGG
GACACAAGAGCTTCCCCAGCGGCCACACATCTTGGTCGTTTGCTGGTCTAGGATTTCTAT
CGTTATACTTGTCTGGGAAAATCAGGGTGTTTGACCAGAGAGGGCATGTTGCAAAGCTCT
GCATTGTGATTTTACCTCTACTGGTTGCAGCATTGGTTGGTGTATCCAGAGTTGATGACT
ATTGGCATCACTGGCAAGATGTTTTTGGAGGAGCTATCATAGGATTGACTGTGGCCACAT
TTTGTTATCTGCAATTTTTCCCTCCTCCATACGATCCAGACGGTTGGGGACCTCATGCCT
ACTTCCAGATGCTGGCAGACTCAAGAAATGATGTCCAAGATTCAGCAGGAATGAATCATC
TAAGCGTGAGGCAAACAGAGCTAGAGAGCGTACGTTGATGGAGAAGAGACGTCCATGGAA
ATATCAAGAAGCAACACGCGGGACACCACCCGTATGCTTCAGAACCGCTAAGTGAAGTCT
TTGTACTCGTTATCTATCAATCTTAGGCATTGTCGCATTGATATGTATTGGCTTAATCAC
AAGGCCCAATATTGGTTGGAAGCCCATTCGCT
```

Figure 2

CCCACGCGTCCGCCACATTTCTCTTTAACCTCATCTCATCTCTTAGTCGAGATC
TTCACTTTCTGATGACAATAGGGTCGTTTTCTCTTCTCTCTTATTCTGGCGCA
ATTCTCAGGACCAGGAGGCGCAGAGAGGGAGGATGCAGGAGATAGATCTTA
GTGTTCACACTATAAAGTCCCATGGAGGAAGAGTCGCTTCTAAACACAAGCA
CGATTGGATCATACTCGTCATCTTGATTGCCATCGAGATAGGCTTGAACCTCA
TCTCTCCTTTCTACCGCTACGTGGGAAAAGACATGATGACTGACCTCAAGTAC
CCTTTCAAGGACAACACCGTACCTATCTGGTCTGTCCCTGTGTACGCTGTGCT
TCTTCCCATCATAGTGTTCGTCTGCTTCTACCTGAAGAGGACATGTGTGTACG
ATCTGCACCACAGCATCCTCGGGCTGCTCTTCGCCGTCTTGATAACTGGTGTC
ATCACTGACTCCATCAAGGTAGCCACCGGACGCCCTCGTCCTAACTTCTACTG
GCGCTGCTTCCCCGACGGCAAAGAGCTGTATGATGCGTTGGGAGGTGTGGTA
TGCCACGGCAAGGCAGCTGAGGTCAAGGAAGGCCACAAGAGCTTCCCGAGC
GGACACACTTCCTGGTCCTTTGCGGGGCTTACATTCCTTTCCCTTTACCTCTCT
GGCAAAATCAAGGCCTTCAACAATGAAGGACATGTGGCGAAACTCTGCCTCG
TGATCTTCCCTCTGCTTGCCGCTTGTCTTGTGGGGATATCTCGTGTGGATGACT
ACTGGCACCACTGGCAAGATGTCTTCGCAGGAGCTCTCATTGGCACCCTTGTA
GCCGCCTTCTGCTACCGTCAGTTCTACCCCAACCCTTACCACGAAGAAGGATG
GGGTCCCTACGCCTATTTCAAGGCAGCTCAAGAACGAGGAGTCCCTGTGACC
TCCTCCCAAAACGGAGATGCCTTGAGGGCTATGTCTCTGCAGATGGATTCAA
CATCTCTCGAAAACATGGAATCTGGCACTTCCACCGCTCCCAGATGATCCTCC
TCTCTTATTATTTGATTCATTATTTGGTTTTTCATTTTGATTTGGCCGTCGTCGT
GAGATTGTGAATGGTGTAGCTACATACTGTATGTGTATTCAAAACTCTACTTG
TACCATTACATTTTTGTAAATCCACTCTTCATGAAATTGACGTTAAAAAAAA
AAAAAA

Figure 3

```
GCGTCCGATCGACTAGAGTCTGCACAGGATGAGAGAGGCACAGCTAGGCGGTCACACTCT
GAGGTCCCATGGAATGACTGTTGCAAGGACTCACATGCATGATTGGATCATTCTCGTGTT
ACTTGTTATTCTCGAGTGTGTACTCCTTATAATCCACCCATTTTATCGCTTTGTTGGTAA
AGATATGATGACTGATCTAAGTTACCCGTTAAAGAGTAACACCGTACCAATTTGGTCTGT
CCCGGTATATGCGATGCTGTTACCTTTGGTAATCTTCATCTTTATCTACTTCCGTCGAAG
AGATGTTTATGATCTTCATCACGCGGTGCTAGGTCTCTTATACTCTGTTCTGGTGACAGC
AGTACTTACCGATGCAATAAAGAATGCAGTTGGTCGACCACGTCCTGACTTCTTCTGGCG
TTGTTTTCCAGATGGCAAAGCTCTTTATGATAGCCTTGGAGATGTTATATGCCATGGTGA
TAAAAGCGTCATAAGGGAAGGTCACAAAAGCTTTCCAAGTGGACACACGTCATGGTCTTT
TTCGGGTCTCGGATTTCTTTCGCTTTACTTATCGGGAAGATTCAAGCATTTGACGGTAA
AGGCCACGTTGCAAAGCTATGCATAGTCATACTCCCTTTGCTATTTGCAGCTCTTGTCGG
CATTTCCCGTGTTGATGACTATTGGCATCATTGGCAAGACGTCTTTGCAGGAGGCTTGCT
AGGTCTTGCGATCTCTACAATCTGTTATCTTCAATTTTTCCCGCCACCATATCACACCGA
AGGTTGGGGACCATATGCTTACTTCCAAGTGTTGGAGGCTGCGAGAGTGCAAGGAGCAGC
GAATGGAGCAGTGCAGCAGCCGCCGCCCCAAGTTAACAACGGTGAAGAAGAAGACGGTGG
GTTTATGGGTTTACATTTGGTGGATAATCCGACTATGAGGAGAGAAGAGGATGTAGAAAC
TGGTAGAGGCTGAGATGAAGAAACTCTGAAGCTGGTTTGGTTACTTGTTAGGACACTTTC
TCTTGTTCTTTTGATTCTTTGTTGGACAACTTTAGTAGATTTCTCTAAGATAACTAATAG
AGTCGTTTGGTTTTAAAAAAAAAAAAAAAAAAA
```

Figure 4

```
TGATATGCCATGGTGATAAAAGTGTCATAAGTGAAGGGCACAAAAGCTTCCCAAGCGGAC
ACACCTCTTGGTCTTTTGCGGGTCTAGGATTCTTGTCGCTGTATTTATCAGGGAAGATTC
AAGCGTTTCATGGTAAAGGCCACGTTGCGAACGTATGCATTGTCATACTCCCTTTGCATG
TTGCAGCTCTTGTCGGATTTCCGTGTAGATGACTATGGCATTCACTGGCAGACGCTTTGC
TGGAGGCTGCTAGG
```

Figure 5

```
GTCGACCCACGCGTCCGCCCACGCGTCCGCGGACGCGTGGGCGCTAGCAGCGGCGGCGCC
GGCAGTTGGTAGCCGCGACCGAGACACGGCGGGTGACCTGCCCCGCCGCAGTCGGGGTGT
ATGTATTACCACCGCCAGAATTCCAGGAGACAATGGCAGACCAGTTAGGGTCTTACACTA
TTAGATCCATGGAATGATATTGGCAAGGTTGCACATGTATGACTGGATAATACTTCTCC
TCCTTGCTGTCATAGACGGGCTGTTGAATATAATTGAACCATTTCACCGTTTTGTTGGGA
AAGACATGATGACTGACTTGAGATATCCTATGAAGGGCAATACAGTGCCATTTTGGGCTG
TTCCACTGATTGGAATTATACTGCCTTGGGCCATCTTTGTTGGGATTTACTTCAAAAAGA
AGAATTTTTATGATTTGCACCATGGCATACTGGGGATTCTATACTCAGTGCTGATAACTG
CAGTGATTACTGATGCAATTAAGGATGGTGTTGGACGGCCTCGTCCAGATTTTTTCTGGC
GCTGTTTCCCTAATGGAAATGATGTTTATGATAACATTACTACTGGTGTTATATGCAATG
GAGTGAAGAGCGTAATCAAGGAAGGCCACAAGAGCTTTCCCAGTGGACACAGTTCATGGT
CTTTTGCTGGTCTAGGCTTCCTTGCATGGTACTTAGCTGGGAAACTCACAGCCTTTGACC
GCAAAGGGCATATTGCGAAGCTATGCATTGTGTTCCTGCCTCTCCTTACTGCCGCACTTG
TGGCTGTTTCTCGAGTGGACGACTACTGGCATCATTGGCAAGATGTATTTGCAGGGGGTC
TTATAGGTCTTACAGTTGCTTCGTTTTGCTACCTACAGTTTTTCCCATATCCTTTCGATG
GCGATGCTTTGTGGCCTCACGCATACGCGGTCCGGTTAGCCGAGGAGGGGAACAGCAGAA
ATGCGAACTCGTACAGCGTGAGACCAACCGAGATCGAAACAGTCGATATTCCTGGGCACG
GTGCGATCATCACCCAAGAGAGACTCTAAACGATGTGGAGTCTGGCAGTGCCAGGAGAT
TGTGAGATGGGTCTGCAGGTGTGGAGATTGATGTCTCAGATACCATGGGAGTTGCTTGCA
TATGTGTACAGGTAGATCTATTGTAGAGCTGTTGACTGCTGCCACCGTGATAGGGAGGG
TTGCTTAGACGGGCCTGGCAGTAAATTTACTTGGTAGGGGTGCTGTTTCTTCTGAGAACC
TTTGGCTTTTGTTTGTATATATACTCTTATCAAAGTGTTTGCTGACACTTTTGTAACCAG
TTTGGTCGCTGCATTCAGCAACTATGATCAAAAAAAAAAAAAAAAAAAAAAAAAAAAAAG
GGCGGCCGC
```

Figure 6

```
CTCGAGTTGATATTCCCAATCTCTCTGTTTCTATTTCTTTGTTCGTTGCTTCACACTATG
GCTTCTTGGTGGGATTTAAGACCCTTCTTTCGTTTTCAGTCTGTTAGGACCCGATTTCAG
GAATTCAGGACGAGGGAAGTCCAACTTGGTTCACATACTGTGAGTTCTCATGGATATGCA
GTTGCAAGAACACACAAACATGATTGGCTCATTCTCTTGCTCCTCGTGTTGATTGTTATC
AGCCTGTACATTATCCATCCTTTCCATCGCTTTGTTGGGAAGGATATGATGACTGATCTC
AAATATCCACTGAAGAGTAATACAGTTCCTGCTTGGGCTATTCCTATATATGCAATTTTA
TTGCCCATAGTGATCTTTCTTGGTGTCTACATCCGAAGGAGAGACGTCTATGATCTTCAT
CATGCTGTGCTGGGTTTATTGTTCTCCGTTTTAATAACAGCAGTATTTACTGAGGCAATA
AAAAATGCAGTAGGTCGACCTCGACCAGACTTCTTCTGGCGATGTTTTCCAGATGGAAAG
GATGTTTATGATAAATGGGGAGATGTCATTTGTCATGGTGACCAAAAGGTCATAAAGGAA
GGATACAAGAGTTTCCCAAGTGGTCATACTTCAGGGTCATTTTCTGGTCTGGGTTTTTTA
TCATTGTACTTATCTGGAAAAATAAAAGCATTTGATCGCAAAGGTCATGTTGCAAAACTT
TGCATTGTTTTTCTACCACTACTTGTTGCATCACTTGTTGGCATTTCTCGAGTTGATGAC
TACTGGCACCACTGGCAAGACGTGTTTGCGGGAGGTCTTTTAGGGCTTACAGTGGCTACA
TTTTGCTATTTGCAGTTTTTTCCTCCTCCTTATCATTCTGAAGGCTGGGGTCCTTATGCG
TATTTTAGGATGTTGGAAGAATCTCGTGGTATGACCCAAGTTCCTAGTGTTCAAAATTCT
GGTCAAGCGCAGTTAGCAGAGGCTCAGGCTGAGAGCCAAGAGGAACAAGGTCTCCACGGG
TGTATGGGGTTAACTTTATCACGGGATCATCATGCAGCATTGAATGACTGTGAATCTGGG
AGGGGATAAAGTCTGTACATTTCATGATCTTGCTCTCTGTAAAATGTAAATCAGATGTTA
GTTCGTAGCCTAGGATTTTAACCAGTATTTAAAACTAACACATTTTGTTGAATAGTTGTT
TCTATTCAGTCACTAGTGTCTCTGAAAACTTTGAAGCGTAGTTGTTTGTAAGAGTCAGGT
TTGGGACAATTAACCTTTGTTATTTCAATATTTTGTGAATATGTTGACATAAGAAAATAC
GAAATCTCTTGAGAAGATTGCCGTTCATTCAAAAAAAAAAAAAA
```

Figure 7

```
CTCGAGCCTCGAATCTCGTGCACGTGCCGTTGCAGCAAAAAATGCCAGAAATTCAGTTGG
GTATGCATACTATCAGATCACATGGAACTAGAGTGGCAAGGACACATATGCACGACTGGT
TGATTCTTTTGCTTCTTGTGATCATCGATGCTGTCTTGAATTTAATACAGCCATTTCACC
GTTTTGTTGGAGAGGGGATGATGACAGACCTTAGATACCCATTGAAAGCTAATACAATTC
CCTTTTGGGCTGTTCCGATAATAGCAATATTGTTACCACTGGCTGTTTTTCTCGTTTACT
ATTTCATTCGTAAGGATGTCTATGACCTCCACCATGCTATAATGGGCCTTCTATTTTCTG
TACTCATTACTGCGGTGATGACTGATGCTATCAAGGATGCTGTTGGACGGCCAAGGCCAG
ACTTCTTCTGGCGTTGTTTCCCTGATGGAAAAGGGGTGTTTGATCCAGTAACAAGTAATG
TTCTGTGTACTGGAGATAAGGGTGTTATTAAGGAAGGGCACAAAAGTTTCCCCAGTGGAC
ATACCTCTTGGTCCTTTGCTGGTCTTGTTTATCTTGCTTGGTATCTATCTGGAAAACTTA
GGGCATTTGACCGCAGGGGCATGTTGCAAAGCTCTGTCTTGTTTTCTTACCAATCCTCG
TGGCAGCTATGATTGCTGTCTCTCGTGTTGATGATTACTGGCATCATTGGCAAGATGTGT
TTGCTGGAGCTCTTATAGGGATGATAATTGCTTCATTTTGTTACTTACAATTCTTTCCAC
CTCCATATGACGTAGATGGTTGGGGACCTCATGCATATTTCCAGATGTTGGCTGAATCTC
GTAATGGTGCTCAGCCCTCTACTGTCAATAATGAGATTCATCATGTCCAATCTGCTGAGC
TTCAGGCTGTATCTTTGTATATCCCACCTCAACATGATGCAGATACACGAGGCAATAGCT
GGGATTCAAGCCCCATGTTAGGTGCATCCCAAAATGTAAGAACACACTGACGACATAGGA
AAGATCACCAACATGTCCATAATCTGTAAAAATTATAGGAGGGATTCGTTGCAGATAAAC
CACTTTAGCATTGTTGGTGGTTTAAAATGCGGATATCAATCAATTTCTTTGCTTGTTGGA
TTGGAAATTTGGGATGCCATGTTAGTTGTCTTTAATTTTCCGGCCAGCTTATATTTGTTA
GTTGTCAAAGCACTGTTTCTATACAGAGAATGATTTAATCGGCTCAACAGGATTCAAGCA
AAAAAAAAAAAAAAA
```

Figure 8

SEQUENCE LISTING

<160> NUMBER OF SEQ ID NOS: 18

<210> SEQ ID NO 1
<211> LENGTH: 154
<212> TYPE: DNA
<213> ORGANISM: Homo sapiens
<220> FEATURE:
<221> NAME/KEY: unsure
<222> LOCATION: (1)..(154)
<223> OTHER INFORMATION: unsure at all n locations

<400> SEQUENCE: 1

| | | | | | |
|---|---|---|---|---|---:|
| mnykydkavs | knggsannnr | rsgskrvcdc | magtstkyhr | gycndskykt | gtndavcavg | 60 |
| vaatgyryyk | ksrstnyvaa | ykvgcgcass | tdakvsgrrh | svcndsncsg | ynyrcrgdds | 120 |
| kvarkssgha | ssmytmyvya | rtwrgarcsg | scss | | | 154 |

<210> SEQ ID NO 2
<211> LENGTH: 188
<212> TYPE: DNA
<213> ORGANISM: Mus musculus
<220> FEATURE:
<221> NAME/KEY: unsure
<222> LOCATION: (1)..(188)
<223> OTHER INFORMATION: unsure at all n locations

<400> SEQUENCE: 2

| | | | | | |
|---|---|---|---|---|---:|
| mdktryvadv | cvagatsrht | rgcnddskyy | kdtyaggvcv | msgssvynvh | snsvgnyaty | 60 |
| kavgagvsas | stdakytgsr | hacndwsknc | sdgydycgnk | vkgrsysghs | ssmycmvaya | 120 |
| rmkgdwarrm | gasyvgsrvs | dykhhwsdvt | vggaamavay | vsdkdthsyk | rkdhtthtas | 180 |
| srnystnh | | | | | | 188 |

<210> SEQ ID NO 3
<211> LENGTH: 186
<212> TYPE: DNA
<213> ORGANISM: Rattus sp.
<220> FEATURE:
<221> NAME/KEY: unsure
<222> LOCATION: (1)..(186)
<223> OTHER INFORMATION: unsure at all n locations

<400> SEQUENCE: 3

| | | | | | |
|---|---|---|---|---|---:|
| mdkryvvdvc | vagtsrhtrg | vctdskyyrd | tyaggvcvmt | gtsvynvhsn | svsnhyatyk | 60 |
| avgagasass | tdakysgrrh | avcndwsknc | sdgynvcgnk | vrgrsysghs | ssmycmvaya | 120 |
| rmkgdwarrm | gvasyvgsrv | sdykhhwsdv | ggavvavvyv | tdkttsnkrk | dshtthttnr | 180 |
| syarnh | | | | | | 186 |

<210> SEQ ID NO 4
<211> LENGTH: 165
<212> TYPE: DNA
<213> ORGANISM: Saccharomyces cerevisiae
<220> FEATURE:
<221> NAME/KEY: unsure
<222> LOCATION: (1)..(165)
<223> OTHER INFORMATION: unsure at all n locations

<400> SEQUENCE: 4

| | | | | | |
|---|---|---|---|---|---:|
| mnrvsktnga | kwrdvmnyvy | yryndtshya | ttrvnnnmvy | svvstgsadr | rhytsgsaws | 60 |
| tstnknwgrr | ddrcvgdtta | kdvcttknhr | dgrttsghss | saggyywcgt | smwrkmvaga | 120 |
| aasrtdyrhh | vdvgsmgyma | hyrrddkmdd | sdvtavthrd | hsdgm | | 165 |

<210> SEQ ID NO 5
<211> LENGTH: 1232
<212> TYPE: DNA
<213> ORGANISM: Arabidopsis thaliana

<400> SEQUENCE: 5

| | | | | | |
|---|---|---|---|---|---|
| caaaaaactt | tatctttcct | tcctttgaaa | tctcccggag | aaaaactata | gagattttcc | 60 |
| gtttcccgct | ttaatacagt | gccccaattc | gcgcgacaca | tagagtgtag | agacgctttc | 120 |
| acgagcgttt | ccgacgtcgg | actttcagct | catcatctcc | acatctttaa | cggtaaagat | 180 |
| taatcatgcc | tgaaattcat | ttgggtgctc | atacaataag | atcccatgga | gtaacagtcg | 240 |
| cgaggttcca | catgcatgac | tggctcattc | ttctgctgct | aatagtcatt | gaaattgttc | 300 |
| ttaatgtcat | cgaacccttt | catcgttttg | ttggagaaga | tatgctcact | gatctcagat | 360 |
| accctctgca | ggacaacaca | attccttct | gggctgtccc | gttgatagct | gttgtgctac | 420 |
| cttttgctgt | catttgtgtt | tactacttca | ttagaaatga | tgtttatgac | ctgcatcatg | 480 |
| caatactagg | gcttttgttc | tctgtactta | taaccggtgt | cataaccgat | gctataaagg | 540 |
| acgctgttgg | tcgacctcgt | cctgatttct | tttggcgttg | tttccctgac | ggtataggga | 600 |
| tctttcacaa | tgtcacgaag | aatgttctat | gtactggagc | taaggatgtg | gtcaaagagg | 660 |
| gacacaagag | cttccccagc | ggccacacat | cttggtcgtt | tgctggtcta | ggatttctat | 720 |
| cgttatactg | tctgggaaa | tcagggtgt | tgaccagag | agggcatgtt | gcaaagctct | 780 |
| gcattgtgat | tttacctcta | ctggttgcag | cattggttgg | tgtatccaga | gttgatgact | 840 |
| attggcatca | ctggcaagat | gttttttggag | gagctatcat | aggattgact | gtggccacat | 900 |
| tttgttatct | gcaattttc | cctcctccat | acgatccaga | cggttgggga | cctcatgcct | 960 |
| acttccagat | gctggcagac | tcaagaaatg | atgtccaaga | ttcagcagga | atgaatcatc | 1020 |
| taagcgtgag | gcaaacagag | ctagagagcg | tacgttgatg | gagaagagac | gtccatggaa | 1080 |
| atatcaagaa | gcaacacgcg | ggacaccacc | cgtatgcttc | agaaccgcta | agtgaagtct | 1140 |
| ttgtactcgt | tatctatcaa | tcttaggcat | tgtcgcattg | atatgtattg | gcttaatcac | 1200 |
| aaggcccaat | attggttgga | agcccattcg | ct | | | 1232 |

<210> SEQ ID NO 6
<211> LENGTH: 1222
<212> TYPE: DNA
<213> ORGANISM: Arabidopsis thaliana

<400> SEQUENCE: 6

| | | | | | |
|---|---|---|---|---|---|
| cccacgcgtc | cgccacattt | ctctttaacc | tcatctcatc | tcttagtcga | gatcttcact | 60 |
| ttctgatgac | aatagggtcg | ttttttctctt | ctctcttatt | ctggcgcaat | tctcaggacc | 120 |
| aggaggcgca | gagagggagg | atgcaggaga | tagatcttag | tgttcacact | ataaagtccc | 180 |
| atggaggaag | agtcgcttct | aaacacaagc | acgattggat | catactcgtc | atcttgattg | 240 |
| ccatcgagat | aggcttgaac | ctcatctctc | ctttctaccg | ctacgtggga | aaagacatga | 300 |
| tgactgacct | caagtaccct | ttcaaggaca | acaccgtacc | tatctggtct | gtccctgtgt | 360 |
| acgctgtgct | tcttcccatc | atagtgttcg | tctgcttcta | cctgaagagg | acatgtgtgt | 420 |
| acgatctgca | ccacagcatc | ctcgggctgc | tcttcgccgt | cttgataact | ggtgtcatca | 480 |
| ctgactccat | caaggtagcc | accggacgcc | tcgtcctaa | cttctactgg | cgctgcttcc | 540 |
| ccgacggcaa | agagctgtat | gatgcgttgg | gaggtgtggt | atgccacggc | aaggcagctg | 600 |

| | |
|---|---|
| aggtcaagga aggccacaag agcttcccga gcggacacac ttcctggtcc tttgcggggc | 660 |
| ttacattcct ttccctttac ctctctggca aaatcaaggc cttcaacaat gaaggacatg | 720 |
| tggcgaaact ctgcctcgtg atcttccctc tgcttgccgc ttgtcttgtg gggatatctc | 780 |
| gtgtggatga ctactggcac cactggcaag atgtcttcgc aggagctctc attggcaccc | 840 |
| ttgtagccgc cttctgctac cgtcagttct accccaaccc ttaccacgaa gaaggatggg | 900 |
| gtccctacgc ctatttcaag gcagctcaag aacgaggagt ccctgtgacc tcctcccaaa | 960 |
| acggagatgc cttgagggct atgtctctgc agatggattc aacatctctc gaaaacatgg | 1020 |
| aatctggcac ttccaccgct cccagatgat cctcctctct tattatttga ttcattattt | 1080 |
| ggtttttcat tttgatttgg ccgtcgtcgt gagattgtga atggtgtagc tacatactgt | 1140 |
| atgtgtattc aaaactctac ttgtaccatt acattttgt aaatccactc ttcatgaaat | 1200 |
| tgacgttaaa aaaaaaaaa aa | 1222 |

<210> SEQ ID NO 7
<211> LENGTH: 1113
<212> TYPE: DNA
<213> ORGANISM: Arabidopsis thaliana

<400> SEQUENCE: 7

| | |
|---|---|
| gcgtccgatc gactagagtc tgcacaggat gagagaggca cagctaggcg gtcacactct | 60 |
| gaggtcccat ggaatgactg ttgcaaggac tcacatgcat gattggatca ttctcgtgtt | 120 |
| acttgttatt ctcgagtgtg tactccttat aatccaccca ttttatcgct tgttggtaa | 180 |
| agatatgatg actgatctaa gttacccgtt aaagagtaac accgtaccaa tttggtctgt | 240 |
| cccggtatat gcgatgctgt tacctttggt aatcttcatc tttatctact tccgtcgaag | 300 |
| agatgtttat gatcttcatc acgcggtgct aggtctctta tactctgttc tggtgacagc | 360 |
| agtacttacc gatgcaataa agaatgcagt tggtcgacca cgtcctgact tcttctggcg | 420 |
| ttgttttcca gatggcaaag ctctttatga tagccttgga gatgttatat gccatggtga | 480 |
| taaaagcgtc ataagggaag gtcacaaaag ctttccaagt ggacacacgt catggtcttt | 540 |
| ttcgggtctc ggatttcttt cgctttactt atcgggaaag attcaagcat tgacggtaa | 600 |
| aggccacgtt gcaaagctat gcatagtcat actcccttg ctatttgcag ctcttgtcgg | 660 |
| catttcccgt gttgatgact attggcatca ttggcaagac gtcttgcag gaggcttgct | 720 |
| aggtcttgcg atctctacaa tctgttatct tcaatttttc ccgccaccat atcacaccga | 780 |
| aggttgggga ccatatgctt acttccaagt gttggaggct gcgagagtgc aaggagcagc | 840 |
| gaatggagca gtgcagcagc cgccgcccca agttaacaac ggtgaagaag aagacggtgg | 900 |
| gtttatgggt ttacatttgg tggataatcc gactatgagg agagaagagg atgtagaaac | 960 |
| tggtagaggc tgagatgaag aaactctgaa gctggtttgg ttacttgtta ggacactttc | 1020 |
| tcttgttctt ttgattcttt gttggacaac tttagtagat ttctctaaga taactaatag | 1080 |
| agtcgtttgg ttttaaaaaa aaaaaaaaa aaa | 1113 |

<210> SEQ ID NO 8
<211> LENGTH: 254
<212> TYPE: DNA
<213> ORGANISM: Brassica napus

<400> SEQUENCE: 8

| | |
|---|---|
| tgatatgcca tggtgataaa agtgtcataa gtgaagggca caaagcttc ccaagcggac | 60 |
| acacctcttg gtcttttgcg ggtctaggat tcttgtcgct gtatttatca gggaagattc | 120 |

| | |
|---|---|
| aagcgtttca tggtaaaggc cacgttgcga acgtatgcat tgtcatactc cctttgcatg | 180 |
| ttgcagctct tgtcggattt ccgtgtagat gactatggca ttcactggca gacgctttgc | 240 |
| tggaggctgc tagg | 254 |

<210> SEQ ID NO 9
<211> LENGTH: 1389
<212> TYPE: DNA
<213> ORGANISM: Zea mays

<400> SEQUENCE: 9

| | |
|---|---|
| gtcgacccac gcgtccgccc acgcgtccgc ggacgcgtgg gcgctagcag cggcggcgcc | 60 |
| ggcagttggt agccgcgacc gagacacggc gggtgacctg ccccgccgca gtcgggtgt | 120 |
| atgtattacc accgccagaa ttccaggaga caatggcaga ccagttaggg tcttacacta | 180 |
| ttagatccca tggaatgata ttggcaaggt tgcacatgta tgactggata atacttctcc | 240 |
| tccttgctgt catagacggg ctgttgaata taattgaacc atttcaccgt tttgttggga | 300 |
| aagacatgat gactgacttg agatatccta tgaagggcaa tacagtgcca ttttgggctg | 360 |
| ttccactgat tggaattata ctgccttggg ccatctttgt tgggatttac ttcaaaaaga | 420 |
| agaatttta tgatttgcac catggcatac tggggattct atactcagtg ctgataactg | 480 |
| cagtgattac tgatgcaatt aaggatggtg ttggacggcc tcgtccagat tttttctggc | 540 |
| gctgtttccc taatggaaat gatgtttatg ataacattac tactggtgtt atatgcaatg | 600 |
| gagtgaagag cgtaatcaag gaaggccaca agagctttcc cagtggacac agttcatggt | 660 |
| cttttgctgg tctaggcttc cttgcatggt acttagctgg gaaactcaca gcctttgacc | 720 |
| gcaaagggca tattgcgaag ctatgcattg tgttcctgcc tctccttact gccgcacttg | 780 |
| tggctgtttc tcgagtggac gactactggc atcattggca agatgtattt gcaggggggtc | 840 |
| ttataggtct tacagttgct tcgttttgct acctacagtt tttcccatat cctttcgatg | 900 |
| gcgatgcttt gtggcctcac gcatacgcgg tccggttagc cgaggagggg aacagcagaa | 960 |
| atgcgaactc gtacagcgtg agaccaaccg agatcgaaac agtcgatatt cctgggcacg | 1020 |
| gtgcgatcat caccctaaga gagactctaa acgatgtgga gtctggcagt gccaggagat | 1080 |
| tgtgagatgg gtctgcaggt gtggagattg atgtctcaga taccatggga gttgcttgca | 1140 |
| tatgtgtaca ggtagatcta ttgtagagct gttgactgct gccaccgtga taggggaggg | 1200 |
| ttgcttagac gggcctggca gtaaatttac ttggtagggg tgctgtttct tctgagaacc | 1260 |
| tttggctttt gtttgtatat atactcttat caaagtgttt gctgacactt ttgtaaccag | 1320 |
| tttggtcgct gcattcagca actatgatca aaaaaaaaa aaaaaaaaa aaaaaaaag | 1380 |
| ggcggccgc | 1389 |

<210> SEQ ID NO 10
<211> LENGTH: 1364
<212> TYPE: DNA
<213> ORGANISM: Glycine max

<400> SEQUENCE: 10

| | |
|---|---|
| ctcgagttga tattcccaat ctctctgttt ctatttcttt gttcgttgct tcacactatg | 60 |
| gcttcttggt gggatttaag acccttcttt cgttttcagt ctgttaggac ccgatttcag | 120 |
| gaattcagga cgagggaagt ccaacttggt tcacatactg tgagttctca tggatatgca | 180 |
| gttgcaagaa cacacaaaca tgattggctc attctcttgc tcctcgtgtt gattgttatc | 240 |

-continued

```
agcctgtaca ttatccatcc tttccatcgc tttgttggga aggatatgat gactgatctc      300
aaatatccac tgaagagtaa tacagttcct gcttgggcta ttcctatata tgcaatttta      360
ttgcccatag tgatctttct tggtgtctac atccgaagga gagacgtcta tgatcttcat      420
catgctgtgc tgggtttatt gttctccgtt ttaataacag cagtatttac tgaggcaata      480
aaaaatgcag taggtcgacc tcgaccagac ttcttctggc gatgttttcc agatggaaag      540
gatgtttatg ataaatgggg agatgtcatt tgtcatggtg accaaaaggt cataaaggaa      600
ggatacaaga gtttcccaag tggtcatact tcagggtcat tttctggtct gggtttttta      660
tcattgtact tatctggaaa aataaaagca tttgatcgca aaggtcatgt tgcaaaactt      720
tgcattgttt ttctaccact acttgttgca tcacttgttg gcatttctcg agttgatgac      780
tactggcacc actggcaaga cgtgtttgcg ggaggtcttt tagggcttac agtggctaca      840
ttttgctatt tgcagttttt tcctcctcct tatcattctg aaggctgggg tccttatgcg      900
tattttagga tgttggaaga atctcgtggt atgacccaag ttcctagtgt tcaaaattct      960
ggtcaagcgc agttagcaga ggctcaggct gagagccaag aggaacaagg tctccacggg     1020
tgtatggggt taactttatc acgggatcat catgcagcat tgaatgactg tgaatctggg     1080
aggggataaa gtctgtacat ttcatgatct tgctctctgt aaaatgtaaa tcagatgtta     1140
gttcgtagcc taggatttta accagtattt aaaactaaca cattttgttg aatagttgtt     1200
tctattcagt cactagtgtc tctgaaaact ttgaagcgta gttgtttgta agagtcaggt     1260
ttgggacaat taacctttgt tatttcaata ttttgtgaat atgttgacat aagaaaatac     1320
gaaatctctt gagaagattg ccgttcattc aaaaaaaaaa aaaa                      1364
```

<210> SEQ ID NO 11
<211> LENGTH: 1276
<212> TYPE: DNA
<213> ORGANISM: Glycine max

<400> SEQUENCE: 11

```
ctcgagcctc gaatctcgtg cacgtgccgt tgcagcaaaa aatgccagaa attcagttgg       60
gtatgcatac tatcagatca catggaacta gagtggcaag gacacatatg cacgactggt      120
tgattctttt gcttcttgtg atcatcgatg ctgtcttgaa tttaatacag ccatttcacc      180
gttttgttgg agagggatg atgacagacc ttagataccc attgaaagct aatacaattc       240
ccttttgggc tgttccgata tagcaatat tgttaccact ggctgttttt ctcgtttact       300
atttcattcg taaggatgtc tatgacctcc accatgctat aatgggcctt ctattttctg      360
tactcattac tgcggtgatg actgatgcta tcaaggatgc tgttggacgg ccaaggccag      420
acttcttctg gcgttgtttc cctgatggaa aagggggtgtt tgatccagta acaagtaatg     480
ttctgtgtac tggagataag ggtgttatta aggaagggca caaaagtttc cccagtggac      540
atacctcttg gtcctttgct ggtcttgttt atcttgcttg gtatctatct ggaaaactta      600
gggcatttga ccgcaggggg catgttgcaa agctctgtct tgttttctta ccaatcctcg      660
tggcagctat gattgctgtc tctcgtgttg atgattactg gcatcattgg caagatgtgt      720
ttgctggagc tcttataggg atgataattg cttcattttg ttacttacaa ttcttttccac     780 ctccatatga cgtagatggt tggggacctc atgcatattt ccagatgttg gctgaatctc      840
gtaatggtgc tcagccctct actgtcaata atgagattca tcatgtccaa tctgctgagc      900
ttcaggctgt atctttgtat atcccacctc aacatgatga agatacacga ggcaatagct      960
gggattcaag ccccatgtta ggtgcatccc aaaatgtaag aacacactga cgacatagga     1020
```

```
aagatcacca acatgtccat aatctgtaaa aattataggg gggattcgtt gcagataaac    1080
cactttagca ttgttggtgg tttaaaatgc ggatatcaat caatttcttt gcttgttgga    1140
ttggaaattt gggatgccat gttagttgtc tttaattttc cggccagctt atatttgtta    1200
gttgtcaaag cactgtttct atacagagaa tgatttaatc ggctcaacag gattcaagca    1260
aaaaaaaaaa aaaaaa                                                    1276
```

<210> SEQ ID NO 12
<211> LENGTH: 56
<212> TYPE: DNA
<213> ORGANISM: artificial sequence
<220> FEATURE:
<223> OTHER INFORMATION: adapter oligonucleotide

<400> SEQUENCE: 12

```
cgcgatttaa atggcgcgcc ctgcaggcgg ccgcctgcag ggcgcgccat ttaaat         56
```

<210> SEQ ID NO 13
<211> LENGTH: 19
<212> TYPE: PRT
<213> ORGANISM: artificial sequence
<220> FEATURE:
<223> OTHER INFORMATION: conserved region of PAP related amino acid
      sequence
<221> NAME/KEY: unsure
<222> LOCATION: (1)..(19)
<223> OTHER INFORMATION: unsure at all Xaa locations

<400> SEQUENCE: 13

```
Thr Asp Ile Ala Lys Xaa Xaa Ile Gly Arg Leu Arg Pro His Phe Leu Xaa Xaa
1               5                   10                  15
Cys
19
```

<210> SEQ ID NO 14
<211> LENGTH: 14
<212> TYPE: PRT
<213> ORGANISM: artificial sequence
<220> FEATURE:
<223> OTHER INFORMATION: conserved region of PAP related amino acid
      sequence

<400> SEQUENCE: 14

```
Leu Ser Arg Val Ser Asp Tyr Lys His His Trp Ser Asp Val
1               5                   10          14
```

<210> SEQ ID NO 15
<211> LENGTH: 35
<212> TYPE: DNA
<213> ORGANISM: artificial sequence
<220> FEATURE:
<223> OTHER INFORMATION: primer for PCR amplification

<400> SEQUENCE: 15

```
ccagatctgc atgctcaacg tacgctctct agctc                                35
```

<210> SEQ ID NO 16
<211> LENGTH: 38
<212> TYPE: DNA
<213> ORGANISM: artificial sequence
<220> FEATURE:
<223> OTHER INFORMATION: primer for PCR amplification

<400> SEQUENCE: 16

```
ccagatctct cgagacaatg cctgaaattc atttgggt                             38
```

-continued

```
<210> SEQ ID NO 17
<211> LENGTH: 14
<212> TYPE: PRT
<213> ORGANISM: artificial sequence
<220> FEATURE:
<223> OTHER INFORMATION: conserved region depicted in Figure 1
<221> NAME/KEY: unsure
<222> LOCATION: (1)..(14)
<223> OTHER INFORMATION: unsure at all Xaa locations

<400> SEQUENCE: 17

Leu Ser Arg Xaa Xaa Asp Tyr Xaa His His Xaa Xaa Asp Val
1               5                   10              14

<210> SEQ ID NO 18
<211> LENGTH: 323
<212> TYPE: PRT
<213> ORGANISM: artificial sequence
<220> FEATURE:
<223> OTHER INFORMATION: entire conserved region depicted in Figure 1
<221> NAME/KEY: unsure
<222> LOCATION: (1)..(323)
<223> OTHER INFORMATION: unsure at all Xaa locations

<400> SEQUENCE: 18

Xaa Xaa Xaa Xaa Xaa Phe Asp Lys Xaa Xaa Xaa Pro Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Leu Asp Val Xaa Cys Xaa Xaa Xaa Ala Gly
        35                  40                  45

Leu Pro Phe Xaa Ile Xaa Xaa Xaa Xaa Xaa Xaa Xaa Pro Phe Xaa Arg
    50                  55                  60

Gly Xaa Xaa Cys Asn Asp Xaa Ser Ile Lys Tyr Pro Tyr Xaa Xaa Xaa
65                  70                  75                  80

Glu Xaa Thr Ile Xaa Xaa Ala Leu Leu Xaa Xaa Xaa Xaa Ile Xaa Xaa
                85                  90                  95

Xaa Ile Xaa Xaa Xaa Ile Xaa Gly Glu Xaa Leu Xaa Xaa Tyr Xaa Xaa
            100                 105                 110

Xaa Xaa Xaa Ser Xaa Ser Xaa Xaa Xaa Asn Xaa Tyr Ile Ala Xaa Xaa
        115                 120                 125

Tyr Lys Xaa Val Gly Xaa Phe Leu Phe Gly Xaa Xaa Xaa Ser Gln Ser
    130                 135                 140

Xaa Thr Asp Ile Ala Lys Xaa Xaa Ile Gly Arg Leu Arg Pro His Phe
145                 150                 155                 160

Leu Xaa Xaa Cys Asn Pro Asp Xaa Ser Xaa Ile Asn Cys Ser Xaa Gly
                165                 170                 175

Tyr Ile Xaa Xaa Xaa Xaa Cys Xaa Xaa Gly Asn Xaa Xaa Lys Val Xaa
            180                 185                 190

Glu Gly Arg Xaa Ser Phe Xaa Ser Gly His Ser Ser Xaa Xaa Phe Ser
        195                 200                 205

Met Tyr Xaa Met Leu Xaa Xaa Xaa Leu Tyr Leu Gln Ala Arg Xaa Xaa
    210                 215                 220

Xaa Xaa Xaa Ala Arg Leu Xaa Arg Pro Met Xaa Xaa Phe Xaa Xaa Xaa
225                 230                 235                 240

Xaa Xaa Xaa Xaa Xaa Xaa Xaa Leu Ser Arg Xaa Xaa Asp Tyr Xaa His
                245                 250                 255

His Xaa Xaa Asp Val Xaa Xaa Gly Xaa Xaa Xaa Gly Xaa Xaa Xaa Ala
```

-continued

```
                        260                 265                 270
Xaa Xaa Xaa Xaa Xaa Xaa Xaa Xaa Xaa Xaa Xaa Xaa Xaa Xaa Xaa Xaa
            275                 280                 285
Xaa Lys Xaa Xaa Xaa Xaa Xaa Asp Xaa Xaa Xaa Thr Leu Xaa Glu Xaa
    290                 295                 300
Xaa Xaa Xaa Xaa Xaa Xaa Xaa Xaa Xaa Xaa His Xaa Xaa Xaa Xaa
305                 310                 315                 320
Xaa Xaa Xaa
        323
```

PLANT PHOSPHATIDIC ACID PHOSPHATASES

TECHNICAL FIELD

The present invention is directed to nucleic acid and amino acid sequences and constructs, and methods related thereto.

BACKGROUND

Through the development of plant genetic engineering techniques, it is possible to produce a transgenic variety of plant species to provide plants which have novel and desirable characteristics. For example, it is now possible to genetically engineer plants for tolerance to environmental stresses, such as resistance to pathogens and tolerance to herbicides. Another important example for such plant genetic engineering techniques is the production of valuable products in plant tissues, such as improved fatty acid compositions.

There is a need for improved means to obtain or manipulate fatty acid compositions, from biosynthetic or natural plant sources. For example, novel oil products, improved sources of synthetic triacylglycerols (triglycerides), alternative sources of commercial oils, such as tropical oils (i.e., palm kernel and coconut oils), and plant oils found in trace amounts from natural sources are desired for a variety of industrial and food uses.

To this end, the triacylglycerol (TAG) biosynthesis system in mammalian tissues, yeast and plants has been studied. In the cytoplasmic membranes of plant seed tissues which accumulate storage triglycerides ("oil"), fatty acyl groups are added sequentially by specific acyltransferase enzymes to the sn-1, sn-2 and sn-3 positions of glycerol-3-phosphate (G3P) to form TAG. This pathway is commonly referred to as the Kennedy or G3P pathway (FIG. 9).

The first step in TAG formation is the acylation of the sn-1 position of glycerol-3-phosphate (G-3P), catalyzed by glycerophosphate acyltransferase (GPAT), to form lysophosphatidic acid (LA). The lysophosphatidic acid is subsequently acylated at the sn-2 position by lysophosphatidic acid acyltransferase (LPAAT) to create phosphatidic acid.

A key step in the formation of TAG is the dephosphorylation of the sn-3 position of phosphatidic acid (PA) to form sn-1,2-diacylglycerol (DAG) and inorganic phosphate catalyzed by the enzyme phosphatidic acid phosphatase (PAP, EC 3.1.3.4).

The sn-1,2-diacylglycerol is acylated at the sn-3 position by diacylglycerol acyltransferase ultimately forming triacylglycerol (TAG).

The dephosphorylation of phosphatidic acid by PAP is considered to be the rate limiting step of triacylglycerol biosynthesis in animal tissues (Brindley, (1978), *Int. J. Obes.* 2:7–16). Furthermore, in microsomal preparations from developing cotyledons of safflower and sunflower, the inability to form diacylglycerol from phosphatidic acid in reactions of glycerol phosphate and acyl-CoA suggests that PAP may also be the rate limiting step in plants (Stymne, et al., (1987), *The Biochemistry of Plants*, 9:192–193).

Phosphatidic acid phosphatase is also important in the synthesis of substrates involved in the biosynthesis of important membrane phospholipids as DAG can be converted to phosphatidylethanolamine (PE) and phosphatidylcholine (PC) via the CDP-ethanolamine (CDP-Etn)and CDP-choline-based kennedy pathway (Kennedy, et al. (1956) *J. Biol. Chem.* 222:193–214).

In addition, in mammalian cells, PAP is thought to be involved with cellular signal transduction to control the balance between diacylglycerol and phosphatidic acid, which are both secondary messengers in mammalian cell systems.

The characterization of phosphatidic acid phosphatase (also known as PAP) from plants is useful for the further study of plant fatty acid synthesis systems and for the development of novel and/or alternative oils sources. Studies of plant mechanisms may provide means to further enhance, control, modify, or otherwise alter the total fatty acyl composition of triglycerides and oils. Furthermore, the elucidation of the factor(s) critical to the natural production of triglycerides in plants is desired, including the purification of such factors and the characterization of element(s) and/or cofactors which enhance the efficiency of the system. Of particular interest are the nucleic acid sequences of genes encoding proteins which may be useful for applications in genetic engineering.

Relevant Literature

Stymne, et al., (1987), *The Biochemistry of Plants*, 9:192–193 describes phosphatidic acid phosphatase as a rate limiting step in the production of triacylglycerol in plants. Brindley, (1978), *Int. J. Obes.* 2:7–16 describes the rate limiting step of triacylglycerol biosynthesis in animals as the dephosphorylation of phosphatidic acid. Kai, et al. (1996), *J. Biol. Chem.*, 271:18931–18938, describes the cloning of a gene encoding a mouse plasmalemma form of phosphatidic acid phosphatase. Berg, et al. (1997) *Biochemica et Biophysica Acta*, 1330:225–232 describes the purification of a phosphatase which hydrolyzes phosphatidic acid from *Acholeplasma laidlawii*. Carman (1997) *Biochemica et Biophysica Acta* 1348:45–55 describes phosphatidate phosphatases in *Saccharomyces cerevisiae* and *Escherichia coli*.

SUMMARY OF THE INVENTION

Th present invention provides nucleic acid sequences encoding for proteins which catalyze the dephosphorylation of phosphatidic acid (PA) to form sn-1,2-diacylglycerol (DAG). Such proteins are referred to herein as phosphatidic acid phosphatase (EC 3.1.3.4) or PAP.

By this invention, nucleic acid sequences encoding plant PAP may now be characterized with respect to enzyme activity. In particular, isolation of nucleic acid sequences encoding for PAP from Arabidopsis, Brassica, soybean and corn are provided.

Thus, this invention encompasses plant PAP nucleic acid sequences and the corresponding amino acid sequences, and the use of these nucleic acid sequences in the preparation of oligonucleotides containing PAP encoding sequences for analysis and recovery of plant PAP gene sequences. The plant PAP encoding sequence may encode a complete or partial sequence depending upon the intended use. All or a portion of the genomic sequence, or cDNA sequence, is intended.

Of special interest are recombinant DNA constructs which provide for transcription or transcription and translation (expression) of the plant PAP sequences. In particular, constructs which are capable of transcription or transcription and translation in plant host cells are preferred. For some applications a reduction in plant PAP may be desired. Thus, recombinant constructs may be designed having the plant PAP sequences in a reverse orientation for expression of an anti-sense sequence or use of co-suppression, also known as "transwitch", constructs may be useful. Such constructs may contain a variety of regulatory regions including transcriptional initiation regions obtained from genes preferentially expressed in plant seed tissue. For some uses, it may be desired to use the transcriptional and translational initiation regions of the PAP gene either with the PAP encoding sequence or to direct the transcription and translation of a heterologous sequence.

In yet a different aspect, this invention relates to a method for producing a plant PAP in a host cell or progeny thereof via the expression of a construct in the cell. Cells containing a plant PAP as a result of the production of the plant PAP encoding sequence are also contemplated herein.

In addition, methods for increasing oil content in developing seed as well as methods for producing novel oil compositions in developing seeds of oil producing plants are contemplated.

Also considered in this invention are the modified plants, seeds and oils obtained by expression of the plant PAP sequences and proteins of this invention.

BRIEF DESCRIPTION OF THE DRAWINGS

FIG. 2 provides the nucleotide sequence (SEQ ID NO:5) for the Arabidopsis PAP, ATPAP1.

FIG. 3 provides the nucleotide sequence (SEQ ID NO:6) for the Arabidopsis PAP, ATPAP2.

FIG. 4 provides the nucleotide sequence (SEQ ID NO:7) for the Arabidopsis PAP, ATPAP3.

FIG. 5 provides the nucleotide sequence (SEQ ID NO:8) of the Brassica napus PAP EST.

FIG. 6 provides the nucleotide sequence (SEQ ID NO:9) of the corn PAP.

FIG. 7 provides the nucleotide sequence (SEQ ID NO:10) of the soybean (Glycine sp.) soyPAP1.

FIG. 8 provides the nucleotide sequence (SEQ ID NO:11) of the soybean (Glycine sp.) soyPAP2.

DETAILED DESCRIPTION OF THE INVENTION

Figure 1A:
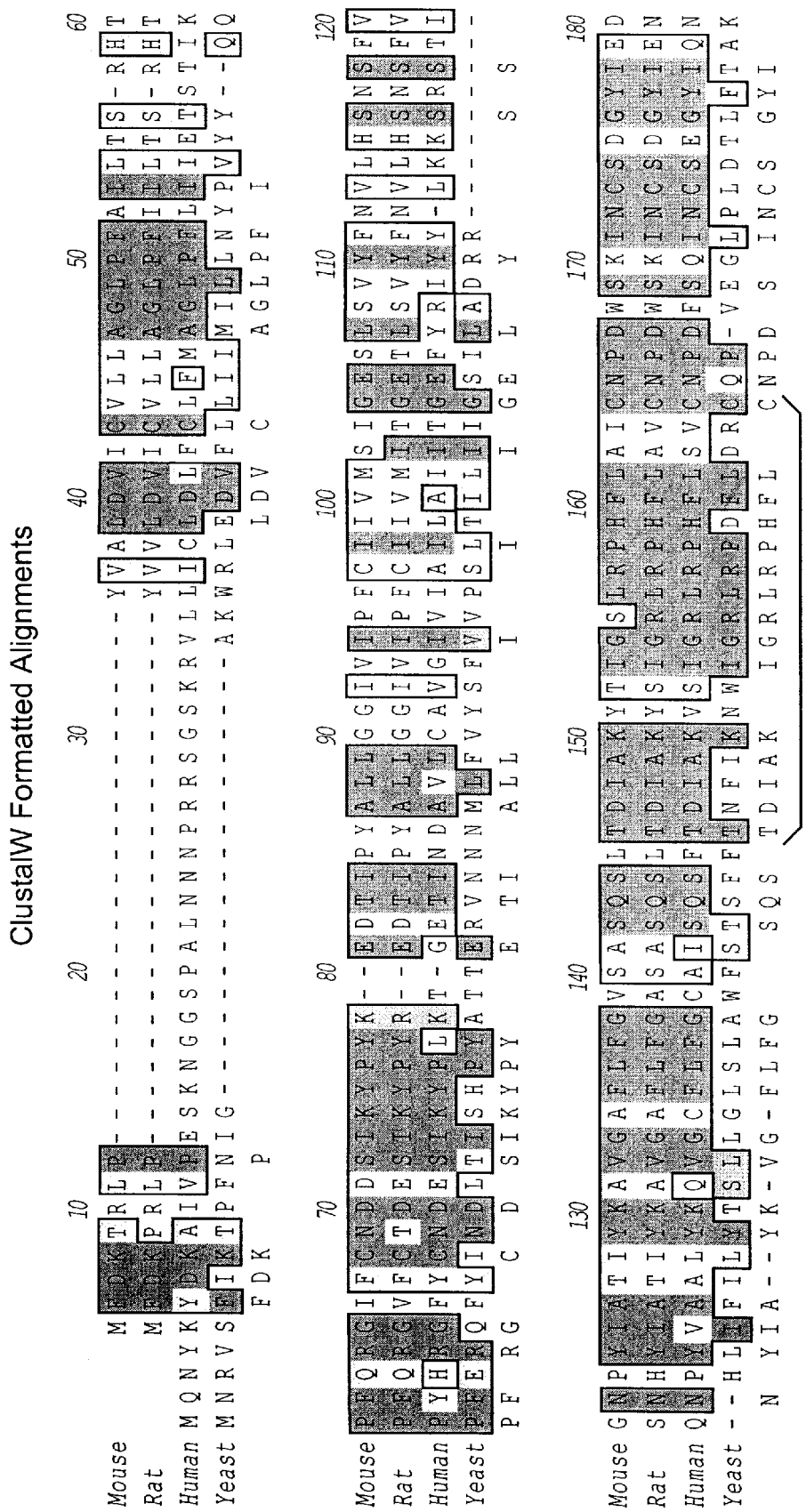
FIG. 1 shows the amino acid sequence alignment of the mouse (SEQ ID NO:2), rat (SEQ ID NO:3), human (SEQ ID NO:1), and yeast (SEQ ID NO:4) PAP related sequences. The underlined sequences show the location of the conserved PAP sequences used to search the databases for plant PAP sequences.
Figure 9:
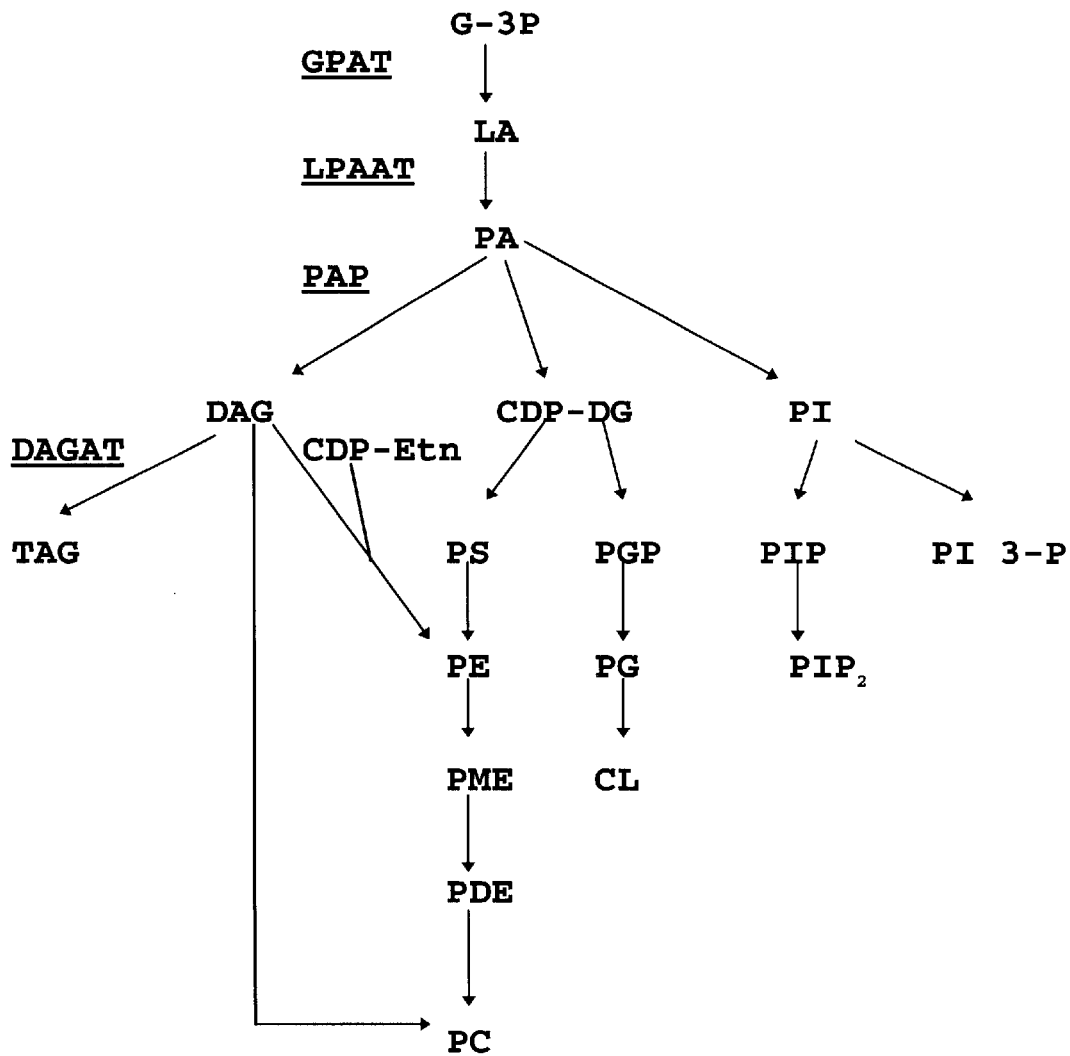
FIG. 9 provides a schematic diagram of the Kennedy pathway for the production of triacylglycerol (TAG) as well as for phosphatidylcholine (PC). G-3P, Glycerol 3 Phosphate; LA, Lysophosphatidic acid; PA, Phosphotidic acid; DAG, Diacylglycerol; TAG, Triacylglycerol; CDP-DG, CDP diacylglycerol; PI Phosphatidylinositol; PS, Phosphatidylserine; PGP, Phosphatidylglycerophosphate; PIP, PI 4-phosphate; P13-P, PI 3-phosphate; PE, Phosphatidylethanolamine; PG, Phosphatidylglycerol; $PIP_2$, PI 4,5-bisphosphate; PME, Phosphatidylmonomethylethanolamine; CL, cardiolipin; PDE, Phosphatidyldimethylethanolamine; PC, Phosphatidylcholine; CDP-Etn, CDP Ethanolamine.

In accordance with the subject invention, nucleic acid sequences are provided which are capable of coding sequences of amino acids, such as, a protein, polypeptide or peptide, obtainable from a plant source, which demonstrates the ability to dephosphorylate phosphatidic acid to form sn-1,2-diacylglycerol under plant enzyme reactive conditions. By "enzyme reactive conditions" is meant that any necessary conditions are available in an environment (i.e., such factors as temperature, pH, lack of inhibiting substances) which will permit the enzyme to function.

In one embodiment of the present invention, nucleic acid sequences are provided which encode for plant phosphatidic acid phosphatase. An *Arabidopsis thaliana* PAP nucleic acid sequence is identified from databases using oligonucleotide sequences derived from conserved sequences of mouse, rat, human, and yeast phosphatidic acid phosphatase amino acid sequences. The Arabidopsis PAP nucleic acid sequence is used to transform yeast, *E. coli* and plants (Arabidopsis and *Brassica napus*) to confirm the identity of the clone.

In order to identify plant phosphatidic acid phosphatase related nucleic acid and amino acid sequences, a known PAP nucleic acid sequence from a mammalian source was used to identify additional PAP nucleic acid sequences from other mammalian and yeast sources. As described in more detail in the following examples, the nucleic acid and amino acid sequence of a mouse plasmalemma form of PAP is used to identify related DNA and protein sequences from public databases. The protein sequences of the PAP related amino acid sequences are compared using protein alignment software applications known in the art. Two amino acid sequences, TDIAKXXIGRLRPHFLXXC (SEQ ID NO:13) and LSRVSDYKHHWSDV (SEQ ID NO:14), are identified which are highly conserved between the different sequences.

These two peptide sequences are used to search a public EST database to identify Arabidopsis cDNAs which contain the conserved sequences. A cDNA clone is identified from the database as containing the sequence LSRVSDYKHHWSDV in two different reading frames.

A full length Arabidopsis PAP nucleic acid sequence is obtained and used to search public and proprietary EST databases. Two additional Arabidopsis PAP related sequences, ATPAP2 (SEQ ID NO: 6) and ATPAP3 (SEQ ID NO: 7), as well as PAP related sequences from corn, soybean, and Brassica are identified. Sequence alignments between the PAP nucleotide sequences demonstrates a high level of identity between the sequences.

Of particular interest in the present invention, is the use of plant PAP genes to increase the oil content of seeds. Stymne et al., (1987, supra) suggests that PAP activity may be a rate limiting step in TAG biosynthesis. Thus, overexpression of a nucleic acid sequence encoding a plant PAP in an oilseed crop may find use in the present invention to increase fatty acid levels in plant tissues.

To confirm the activity and specificity of nucleic acid sequences as PAP enzymes, in vitro assays are performed in *E. coli* and yeast. Expression constructs for *E. coli* and yeast expression are prepared and transformed. Thin Layer Chromotography separation of yeast lipid samples demonstrated the presence of diacylglycerol spots, indicating PAP activity.

All plants utilize PAP proteins in production of TAGs and membrane phospholipids, and thus any given plant species can be considered as a source of additional PAP proteins. Expression of endogenous plant PAP proteins from crop species may find use in the present invention as a method to increase fatty acid compositions in plant tissues. Alternatively, reduced expression of endogenous PAP proteins, for example by using antisense constructs, may find use in the present invention to reduce the levels of membrane lipids in plant tissues.

In another embodiment of the present invention, methods for isolating additional sequences encoding phosphatidic acid phosphatase from other plant species are provided. Such PAP enzymes may find use in producing transgenic plants capable to accumulate high levels of unique oil compositions. For example, identification of a PAP from Cuphea species may have preferential activity for medium-chain phosphatidic acid species. By medium-chain preferring phosphatidic acid species is meant that the enzyme encoded by the PAP nucleic acid sequence demonstrates a preference for dephosphorylating phosphatidic acid species containing C6, C8, C10, C12 and/or C14 fatty acyl groups at the sn-1 and/or sn-2 positions over PA species containing different fatty acyl groups in the sn-1 and/or sn-2 positions.

In addition, identification of a nucleic acid sequence encoding for PAP enzymes from California Bay (*Umbellularia californica*), camphor (*Cinnamomum camphora*), or coconut may also find use in transgenic plants for the increased production of medium-chain fatty acids.

Also of interest in the present invention are PAP enzymes with preferential activity on long chain phosphatidic acid species. Such PAP enzymes may be found in plants such as *Garcinia mangifera* (mangosteen). By long chain preferring phosphatidic acid species is mean that the enzyme encoded by the PAP nucleic acid sequence demonstrates a preference for dephosphorylating phosphatidic acid species containing C16, C18 and/or C18:1 fatty acyl groups at the sn-I and/or sn-2 positions over PA species containing different fatty acyl groups in the sn-1 and/or sn-2 positions.

Alternatively, PAP enzymes with specific activity on very-long chain phosphatidic acid species may find use in the present invention. Such PAP enzymes may be identified in plants such as Nasturtium species, which accumulates over 90% very long chain fatty acids in its seed oil. By very long-chain phosphatidic acid species is meant that the enzyme encoded by the PAP nucleic acid sequence demonstrates a preference for dephosphorylating phosphatidic acid species containing C20, C22 and longer fatty acyl groups at the sn-1 and/or sn-2 positions over PA species containing different fatty acyl groups in the sn-1 and/or sn-2 positions.

Preferential activity of a plant PAP toward particular chain-length fatty acyl-CoA substrates is determined upon comparison of triacylglycerol product amounts obtained per different chain length acyl-CoA donor substrates. In some cases, the chain length of an acyl group in the sn-1 or sn-2 position may affect the ability of the PAP to dephosphorylate the phosphatidic acid.

Alternatively, PAP enzymes from plants which accumulate long-chain fatty acids (C16 and C18 fatty acids) may discriminate against diacylglycerol species containing short-chain, medium-chain or very long-chain fatty acyl groups in the sn-1 and/or sn-2 positions. Thus, PAP enzymes from plants such as Cuphea species, California Bay, or Nasturtium species may not have preferential activity towards certain diacylglycerol species, but may be less discriminatory towards diacylglycerol species containing short-chain, medium-chain or very long-chain fatty acyl groups.

One skilled in the art will readily recognize that antibody preparations, nucleic acid probes (DNA and RNA) and the like may be prepared and used to screen and recover "homologous" or "related" phosphatidic acid phosphatase from a variety of plant sources. Typically, nucleic acid probes are labeled to allow detection, preferably with radioactivity although enzymes or other methods may also be used. For immunological screening methods, antibody preparations either monoclonal or polyclonal may be utilized. Polyclonal antibodies, although less specific, typically are more useful in gene isolation. For detection, the antibody is labeled using radioactivity or any one of a variety of second antibody/enzyme conjugate systems that are commercially available. Examples of some of the available antibody detection systems are described by Oberfilder (*Focus* (1989) BRL Life Technol., Inc., 11:1–5).

In order to obtain additional PAP sequences, a genomic or other appropriate library prepared from the candidate plant source of interest may be probed with conserved sequences from one or more plant PAP(s) to identify homologously related sequences. Positive clones may be analyzed by restriction enzyme digestion and/or sequencing. When a genomic library is used, one or more sequences may be identified providing both the coding region, as well as the transcriptional regulatory elements of the PAP gene from such plant source. Probes can also be considerably shorter than the entire sequence. Oligonucleotides may be used, for example, but should be at least about 10, preferably at least about 15, more preferably at least 20 nucleotides in length. When shorter length regions are used for comparison, a higher degree of sequence identity is required than for longer sequences. Shorter probes are often particularly useful for polymerase chain reactions (PCR), especially when highly conserved sequences can be identified. (See, Gould, et al., *PNAS USA* (1989) 86:1934–1938.)

When longer nucleic acid fragments are employed (>100 bp) as probes, especially when using complete or large cDNA sequences, one can still screen with moderately high stringencies (for example using 50% formamide at 37° C. with minimal washing) in order to obtain signal from the target sample with 20–50% deviation, i.e., homologous sequences. (For additional information regarding screening techniques see Beltz, et al., *Meth. Enzymology* (1983) 100:266–285).

Homologous sequences are found when there is an identity of sequence and may be determined upon comparison of sequence information, nucleic acid or amino acid, or through hybridization reactions between a known PAP and a candidate source. Conservative changes, such as Glu/Asp, Val/Ile, Ser/Thr, Arg/Lys and Gln/Asn may also be considered in determining sequence homology. Typically, a lengthy nucleic acid sequence may show as little as 50–60% sequence identity, and more preferably at least about 70% sequence identity, between the target sequence and the given plant PAP of interest excluding any deletions which may be present, and still be considered related. Amino acid sequences are considered homologous by as little as 25% sequence identity between the two complete mature proteins. (See generally, Doolittle, R. F., OF URFS and ORFS (University Science Books, Calif., 1986.)

In addition, not only can sequences provided herein be used to identify homologous phosphatidic acid phosphatases, but the resulting sequences obtained therefrom may also provide a further method to obtain plant phosphatidic acid phosphatases from other plant sources. In particular, PCR may be a useful technique to obtain related plant PAP from sequence data provided herein. One skilled in the art will be able to design oligonucleotide probes based upon sequence comparisons or regions of typically highly conserved sequence.

Once the nucleic acid sequence is obtained, the transcription, or transcription and translation (expression), of the plant PAP in a host cell is desired to produce a ready source of the enzyme and/or modify the composition of fatty acids and/or triglycerides found therein. Other useful applications may be found when the host cell is a plant host cell, in vitro and in vivo.

Nucleic acids (genomic DNA, plasmid DNA, cDNA, synthetic DNA, mRNA, etc.) encoding phosphatidic acid phosphatase or amino acid sequences of the purified enzymes, which permit design of nucleic acid probes facilitating the isolation of DNA coding sequences therefor, are known in the art and are available for use in the methods of the present invention. It is generally recognized to an artisan skilled in the field to which the present invention pertains that the nucleic acid sequences provided herein and the amino acid sequences derived therefrom may be used to isolate other potential PAP genes from GenBank using DNA and peptide search techniques generally known in the art.

In addition to the sequences described in the present invention, DNA coding sequences useful in the present invention can be derived from algae, fungi, bacteria, mammalian sources, plants, etc. Homology searches in existing databases using signature sequences corresponding to conserved nucleotide and amino acid sequences of PAP can be employed to isolate equivalent, related genes from other sources such as plants and microorganisms. Searches in EST databases can also be employed. Furthermore, the use of DNA sequences encoding enzymes functionally enzymatically equivalent to those disclosed herein, wherein such DNA sequences are degenerate equivalents of the nucleic acid sequences disclosed herein in accordance with the degeneracy of the genetic code, is also encompassed by the present invention. Demonstration of the functionality of coding sequences identified by any of these methods can be carried out by complementation of mutants of appropriate organisms, such as Synechocystis, Shewanella, yeast, Pseudomonas, Rhodobacteria, etc., that lack specific biochemical reactions, or that have been mutated. The sequences of the DNA coding regions can be optimized by gene resynthesis, based on codon usage, for maximum expression in particular hosts.

The nucleic acid sequences which encode plant phosphatidic acid phosphatases may be used in various constructs, for example, as probes to obtain further sequences. Alternatively, these sequences may be used in conjunction with appropriate regulatory sequences to increase levels of the respective PAP of interest in a host cell for recovery or study of the enzyme in vitro or in vivo or to decrease levels of the respective PAP of interest for some applications when the host cell is a plant entity, including plant cells, plant parts (including but not limited to seeds, cuttings or tissues) and plants.

Thus, depending upon the intended use, the constructs may contain the nucleic acid sequence which encodes the entire PAP protein, or a portion thereof. For example, where antisense inhibition of a given PAP protein is desired, the entire PAP sequence is not required. Furthermore, where PAP constructs are intended for use as probes, it may be advantageous to prepare constructs containing only a particular portion of a PAP encoding sequence, for example a sequence which is discovered to encode a highly conserved PAP region.

As discussed above, nucleic acid sequence encoding a plant or other PAP of this invention may include genomic, cDNA or mRNA sequence. By "encoding" is meant that the sequence corresponds to a particular amino acid sequence either in a sense or anti-sense orientation. By "extrachromosomal" is meant that the sequence is outside of the plant genome of which it is naturally associated. By "recombinant" is meant that the sequence contains a genetically engineered modification through manipulation via mutagenesis, restriction enzymes, and the like.

A cDNA sequence may or may not contain pre-processing sequences, such as transit peptide sequences or targeting sequences to facilitate delivery of the PAP protein (such as mitochondrial PAP) to a given organelle or membrane location. The use of any such precursor PAP DNA sequences is preferred for uses in plant cell expression. A genomic PAP sequence may contain the transcription and translation initiation regions, introns, and/or transcript termination regions of the plant PAP, which sequences may be used in a variety of DNA constructs, with or without the PAP structural gene. Thus, nucleic acid sequences corresponding to the plant PAP of this invention may also provide signal sequences useful to direct protein delivery into a particular organellar or membrane location, 5' upstream non-coding regulatory regions (promoters) having useful tissue and timing profiles, 3' downstream non-coding regulatory regions useful as transcriptional and translational regulatory regions, and may lend insight into other features of the gene.

Once the desired plant or other PAP nucleic acid sequence is obtained, it may be manipulated in a variety of ways. Where the sequence involves non-coding flanking regions, the flanking regions may be subjected to resection, mutagenesis, etc. Thus, transitions, transversions, deletions, and insertions may be performed on the naturally occurring sequence. In addition, all or part of the sequence may be synthesized. In the structural gene, one or more codons may be modified to provide for a modified amino acid sequence, or one or more codon mutations may be introduced to provide for a convenient restriction site or other purpose involved with construction or expression. The structural gene may be further modified by employing synthetic adapters, linkers to introduce one or more convenient restriction sites, or the like.

The nucleic acid or amino acid sequences encoding a plant or other PAP of this invention may be combined with other non-native, or "heterologous", sequences in a variety of ways. By "heterologous" sequences is meant any sequence which is not naturally found joined to the native (or wild-type) PAP, including, for example, combinations of nucleic acid sequences from the same plant which are not naturally found joined together.

The DNA sequence encoding a plant or other PAP of this invention may be employed in conjunction with all or part of the gene sequences normally associated with the PAP. In its component parts, a DNA sequence encoding PAP is combined in a DNA construct having, in the 5' to 3' direction of transcription, a transcription initiation control region capable of promoting transcription and translation in a host cell, the DNA sequence encoding plant PAP and a transcription and translation termination region.

Potential host cells include both prokaryotic and eukaryotic cells. A host cell may be unicellular or found in a multicellar differentiated or undifferentiated organism depending upon the intended use. Cells of this invention may be distinguished by having a PAP foreign to the wild-type cell present therein, for example, by having a recombinant nucleic acid construct encoding a plant PAP therein not native to the host species.

Depending upon the host, the regulatory regions will vary, including regions from viral, plasmid or chromosomal genes, or the like. For expression in prokaryotic or eukaryotic microorganisms, particularly unicellular hosts, a wide variety of constitutive or regulatable promoters may be employed. Expression in a microorganism can provide a ready source of the plant enzyme. Among transcriptional initiation regions which have been described are regions from bacterial and yeast hosts, such as *E. coli, B. subtilis, Sacchromyces cerevisiae*, including genes such as beta-galactosidase, T7 polymerase, tryptophan E and the like.

In a preferred embodiment, the constructs will involve regulatory regions functional in plants which provide for modified production of plant PAP, and, possibly, modification of the fatty acid composition. The open reading frame coding for the plant PAP or functional fragment thereof will be joined at its 5' end to a transcription initiation regulatory region. In embodiments wherein the expression of the PAP protein is desired in a plant host, the use of all or part of the complete plant PAP gene is desired; namely all or part of the 5' upstream non-coding regions (promoter) together with the structural gene sequence and 3' downstream non-coding regions may be employed.

If a different promoter is desired, such as a promoter native to the plant host of interest or a modified promoter, i.e., having transcription initiation regions derived from one gene source and translation initiation regions derived from a different gene source, numerous transcription initiation regions are available which provide for a wide variety of constitutive or regulatable, e.g., inducible, transcription of the structural gene functions. The transcription/translation initiation regions corresponding to such structural genes are found immediately 5' upstream to the respective start codons. Among transcriptional initiation regions used for plants are such regions associated with the T-DNA structural genes such as for nopaline and mannopine synthases, the 19S and 35S promoters from CaMV, and the 5' upstream regions from other plant genes such as napin, ACP, SSU, PG, zein, phaseolin E, and the like. Enhanced promoters, such as double 35S, are also available for expression of PAP sequences. For such applications when 5' upstream non-coding regions are obtained from other genes regulated during seed maturation, those preferentially expressed in plant embryo tissue, such as ACP and napin-derived transcription initiation control regions, are desired. Such "seed-specific promoters" may be obtained and used in accordance with the teachings of issued U.S. Pat. Nos. 5,608,152 and 5,530,194, which references are hereby incorporated by reference. Transcription initiation regions which are preferentially expressed in seed tissue, i.e., which are undetectable in other plant parts, are considered desirable for TAG modifications in order to minimize any disruptive or adverse effects of the gene product.

Regulatory transcript termination regions may be provided in DNA constructs of this invention as well. Transcript termination regions may be provided by the DNA sequence encoding the plant PAP or a convenient transcription termination region derived from a different gene source, for example, the transcript termination region which is naturally associated with the transcript initiation region. Where the transcript termination region is from a different gene source, it will contain at least about 0.25 kb, preferably about 1–3 kb of sequence 3' to the structural gene from which the termination region is derived.

Plant expression or transcription constructs having a plant PAP as the DNA sequence of interest for increased or decreased expression thereof may be employed with a wide variety of plant life, particularly, plant life involved in the production of vegetable oils for edible and industrial uses. Most especially preferred are temperate oilseed crops. Plants of interest include, but are not limited to, rapeseed (Canola and High Erucic Acid varieties), sunflower, safflower, cotton, soybean, peanut, coconut and oil palms, and corn. Depending on the method for introducing the recombinant constructs into the host cell, other DNA sequences may be required. Importantly, this invention is applicable to dicotyledenous and monocotyledenous species alike and will be readily applicable to new and/or improved transformation and regulation techniques.

Likewise, the expression of any PAP which is capable of preferentially dephosphorylating a phosphatidic acid containing a medium-chain fatty acyl group in the sn-2 position is also desired for applications in crop species engineered to contain medium-chain fatty acids.

Further plant genetic engineering applications for PAP proteins of this invention include their use in preparation of structured plant lipids which contain TAG molecules having desirable fatty acyl groups incorporated into particular positions on the TAG molecules. For example, in Brassica plants, the sn-2 position of TAG contains mainly unsaturated fatty acyl groups. In certain applications, it may be desirable to have saturated fatty acids at the sn-2 position, and thus a PAP from a different plant source may be identified as having preferential activity on specific phosphatidic acid substrates, for example 16:0 or 18:0 in the sn-2 position, and used for transformation of Brassica.

In addition, in Brassica plants which contain high levels of erucic acid (22:1) in their seed oils (high erucic acid rapeseed or HEAR), little or no 22:1 is found in the sn-2 position of the TAG molecules. A "tri-erucic" HEAR plant having 22:1 in all three of the TAG sn positions is desirable. Such a seed oil may be obtained by expression of a PAP which is preferentially active on phosphatidic acid species containing 22:1 in the sn-2 position in HEAR plants. A gene encoding such an PAP may be identified from meadowfoam (Limnanthes alba), whose seeds accumulate oil containing erucic acid (22:1) in all three sn positions.

In order to increase TAG biosynthesis, and thereby increasing fatty acids, in a plant tissue, coexpression of a plant or other PAP in a plant tissue with a second gene involved in fatty acid biosynthesis may also find use in the present invention. For example, coexpression of a PAP sequence in plant seed tissue with a DNA sequence encoding for another protein involved in TAG biosynthesis, such as LPAAT (U.S. patent application Ser. No. 07/458,109, the entirety of which is incorporated herein by reference) may increase the flux through the kennedy pathway and increase the total fatty acids produced in the seed tissue. Furthermore, other genes involved in TAG biosynthesis, for example DAGAT may be coexpressed with a PAP encoding sequence of the present invention to increase oil levels in plant tissue.

In addition, coexpression of a PAP sequence of the present invention with a sequence encoding an enzyme involved in fatty acid biosynthesis may also find use in the production of increased levels of plant oils. In particular, coexpression of a PAP sequence with a sequence encoding a medium-chain thioesterase may allow for the increased production of medium-chain fatty acids in a plant oil. Such medium-chain thioesterases are known in the art. Examples of medium-chain thioesterases are described in U.S. Pat. Nos. 5,455,167 and 5,667,997, the entireties of which are incorporated herein by reference.

Any means for producing a plant comprising a PAP gene or both a PAP gene and second oil biosynthesis gene are encompassed by the present invention. For example, the second oil biosynthesis gene of interest can be used to transform a plant at the same time as the PAP encoding sequence either by inclusion of both expression constructs in a single transformation vector or by using separate vectors, each of which express desired genes. The second oil biosynthesis gene can be introduced into a plant which has already been transformed to express a PAP encoding sequence, or alternatively, transformed plants, one expressing a PAP encoding sequence and one expressing a second oil biosynthesis gene, can be crossed to bring the genes together in the same plant.

As mentioned above, phosphatidic acid phosphatase also catalyzes the first commited step in the biosynthesis of important membrane phospholipids phosphatidylethanolamine (PE) and phosphatidylcholine (PC) via the CDP-ethanolamine (CDP-Etn) and CDP-choline-based kennedy pathway (Kennedy, et al. (1956) *J. Biol. Chem.* 222:193–214).

In addition, in mammalian cells, PAP is thought to be involved with cellular signal transduction to control the balance between diacylglycerol and phosphatidic acid, which are both secondary messengers. Thus, constructs to direct the expression of the PAP sequences of the present invention in a plant host cell may find use in altering cellular signal transduction events involving DAG and PA as well as DAG and PA products.

Furthermore, the PAP sequences of the present invention may find use in expression constructs to generate transgenic plants with altered membrane lipids or phospholipid levels in the host plant. As phospholipids are involved in cell signaling, altered phospholipid levels may produce plants which have an altered cellular metabolism.

Furthermore, for increased production of a particular chain length fatty acid, for example medium-chain fatty acids, coexpression of a plant or other PAP in a plant tissue with a second DNA sequence encoding for enzymes involved in the production of medium-chain, or other chain length, fatty acids may find use in the present invention. DNA sequences encoding for thioesterases (for example U.S. Pat. No. 5,298,421, U.S. Pat. No. 5,667,997 the entirety of which are incorporated herein by reference) or fatty acid synthases (U.S. patent application Ser. No. 08/827,828 the entirety of which is incorporated herein by reference) are examples of enzymes involved in the production of various chain length fatty acids.

The method of transformation in obtaining such transgenic plants is not critical to the instant invention, and various methods of plant transformation are currently available. Furthermore, as newer methods become available to transform crops, they may also be directly applied hereunder. For example, many plant species naturally susceptible to Agrobacterium infection may be successfully transformed via tripartite or binary vector methods of Agrobacterium mediated transformation. In many instances, it will be desirable to have the construct bordered on one or both sides by T-DNA, particularly having the left and right borders, more particularly the right border. This is particularly useful when the construct uses A. tumefaciens or *A. rhizogenes* as a mode for transformation, although the T-DNA borders may find use with other modes of transformation. In addition, techniques of microinjection, DNA particle bombardment, and electroporation have been developed which allow for the transformation of various monocot and dicot plant species.

Normally, included with the DNA construct will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Depending upon the number of different host species the expression construct or components thereof are introduced, one or more markers may be employed, where different conditions for selection are used for the different hosts.

Where Agrobacterium is used for plant cell transformation, a vector may be used which may be introduced into the Agrobacterium host for homologous recombination with T-DNA or the Ti- or Ri-plasmid present in the Agrobacterium host. The Ti- or Ri-plasmid containing the T-DNA for recombination may be armed (capable of causing gall formation) or disarmed (incapable of causing gall formation), the latter being permissible, so long as the vir genes are present in the transformed Agrobacterium host. The armed plasmid can give a mixture of normal plant cells and gall.

In some instances where Agrobacterium is used as the vehicle for transforming host plant cells, the expression or transcription construct bordered by the T-DNA border region(s) will be inserted into a broad host range vector capable of replication in *E. coli* and Agrobacterium, there being broad host range vectors described in the literature. Commonly used is pRK2 or derivatives thereof. See, for example, Ditta, et al., (*Proc. Nat. Acad. Sci., U.S.A.* (1980) 77:7347–7351) and EPA 0 120 515, which are incorporated herein by reference. Alternatively, one may insert the sequences to be expressed in plant cells into a vector containing separate replication sequences, one of which stabilizes the vector in *E. coli*, and the other in Agrobacterium. See, for example, McBride and Summerfelt (*Plant Mol. Biol.* (1990) 14:269–276), wherein the pRiHRI (Jouanin, et al., *Mol. Gen. Genet.* (1985) 201:370–374) origin of replication is utilized and provides for added stability of the plant expression vectors in host Agrobacterium cells.

Included with the expression construct and the T-DNA will be one or more markers, which allow for selection of transformed Agrobacterium and transformed plant cells. A number of markers have been developed for use with plant cells, such as resistance to chloramphenicol, kanamycin, the aminoglycoside G418, hygromycin, or the like. The particular marker employed is not essential to this invention, one or another marker being preferred depending on the particular host and the manner of construction.

For transformation of plant cells using Agrobacterium, explants may be combined and incubated with the transformed Agrobacterium for sufficient time for transformation, the bacteria killed, and the plant cells cultured in an appropriate selective medium. Once callus forms, shoot formation can be encouraged by employing the appropriate plant hormones in accordance with known methods and the shoots transferred to rooting medium for regeneration of plants. The plants may then be grown to seed and the seed used to establish repetitive generations and for isolation of vegetable oils.

The invention now being generally described, it will be more readily understood by reference to the following examples which are included for purposes of illustration only and are not intended to limit the present invention.

EXAMPLES

Example 1 Identification of PAP Sequences

1A Identification of an Arabidopsis PAP Sequence

Figure 1B:
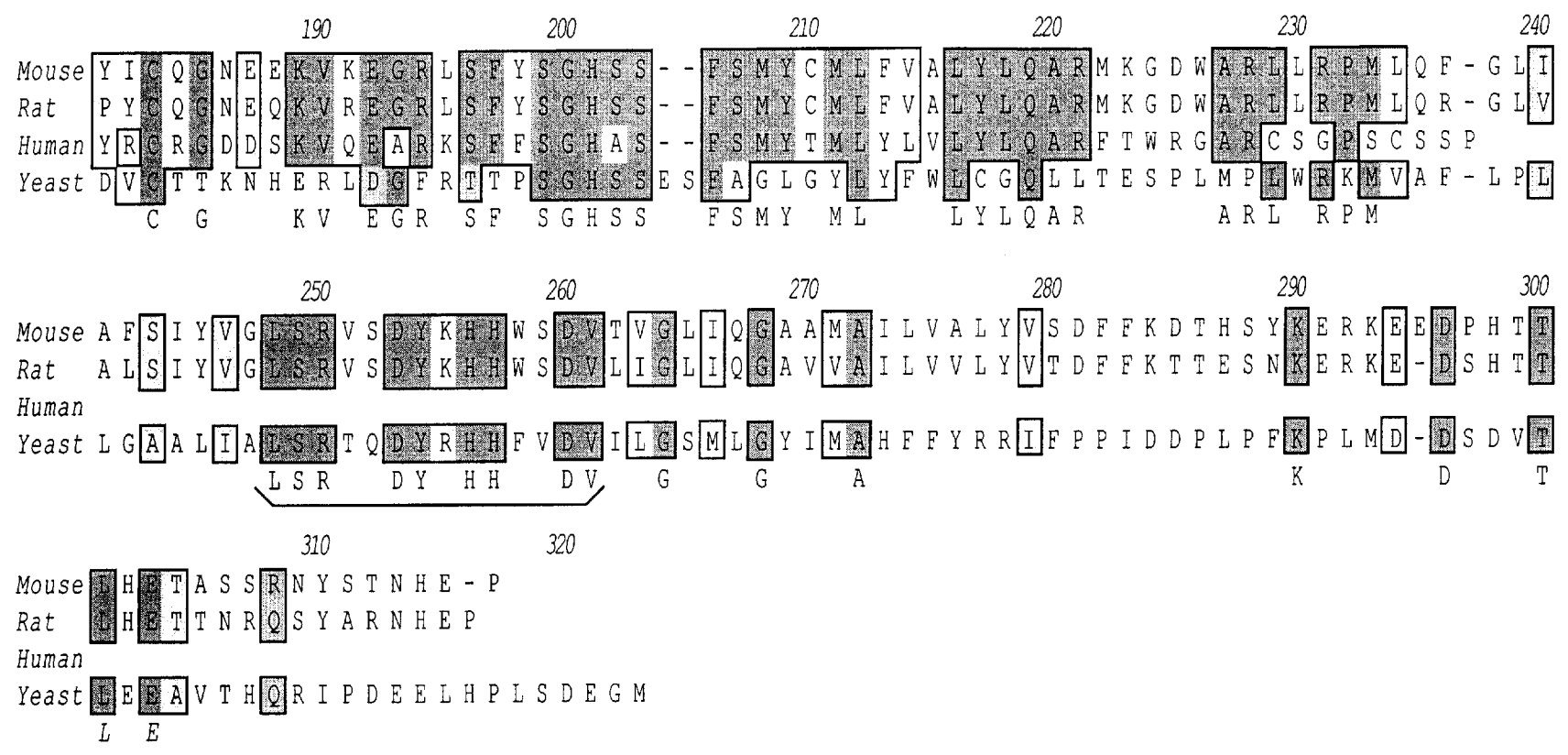

The gene encoding a mouse plasmalemma form of phosphatidic acid phosphatase has been previously cloned and sequenced (Kai, et al. (1996), *J. Biol. Chem.*, 271:18931–18938). The protein sequence was obtained from Genbank and used to search protein and DNA databases to identify related sequences. Sequences from rat, human, C. elegans and yeast were identified as being related to the mouse PAP sequence. The sequences of PAP from mouse (SEQ ID NO: 2), rat (SEQ ID NO: 3), human (SEQ ID NO: 1) and yeast (SEQ ID NO: 4) were aligned (FIG. 1) using Macvector (Oxford Molecular, Inc.), and two conserved peptide sequences were identified; TDIAKXXIGR-LRPHFLXXC (SEQ ID NO:13) and LSRVSDYKHH-WSDV (SEQ ID NO:14). These two protein sequences were used to search the Arabidopsis EST database, and one cDNA clone, 158J20XP, was identified as containing an amino acid sequence motif 71% similar to the LSRVSDYKHHWSDV (SEQ ID NO:14) motif.

The cDNA clone of 158J20XP (also referred to as ATPAP1) was obtained from the Arabidopsis Biological Resource Center (Columbus, Ohio). The full length DNA sequence was determined using an ABI automated sequencer and is shown in FIG. 2 (SEQ ID NO:5). Analysis of the DNA sequence using MacVector indicated an 870 base open reading frame that contained the LSRVSDYKH-HWSDV (SEQ ID NO:14) PAP-related motif.

The cDNA sequence of PAP was amplified from ATPAP1 using the Polymerase Chain Reaction (PCR) and cloned into a vector for further manipulations. The cDNA was amplified using the following primers: 5° CCAGATCTGC ATGCTCAACGTACGCTCTCTAGCTC 3' (SEQ ID NO:15) and 5° CCAGATCTCTCGAGACAATGCCT-GAAATTCATTTGGGT 3' (SEQ ID NO:16) using the reaction conditions of 25 cycles of the following: 94° C. for 15 seconds, 47° C. for 30 seconds, 72° C. for 2 minutes using pfu polymerase (Stratagene, La Jolla, Calif.) following the manufacturers instructions.

The nucleotide sequences of the primers were designed according to the sequence obtained from the Arabidopsis EST clone ATAP1. The forward primer containing PAP gene encoding sequence from the 5' end of the cDNA, including the ATG start codon (underlined above) and restriction cloning sites. The reverse primer contains complementary sequence to sequences in the 3' untranslated region and restriction cloning sites.

Following PCR using the Forward and Reverse primers and RNA prepared as described above , the resulting fragment was cloned into digested EcoRV digested pZERO2 (Invitrogen, Carlsbad, CA) to create the plasmid pCGN8521. The nucleotide sequence of the cloned Arabidopsis PAP cDNA was determined to insure that no errors had been introduced in the PCR process.

1B. Identification of Plant PAP Related Sequences

The sequence from ATPAP1 was used to search the EST database, and a Brassica EST was identified (FIG. 5, Genbank accession H74464, clone RRM1 112 SEQ ID NO:8). The identified Brassica EST was aligned with the DNA sequence from ATPAP1 using MacVector. Alignment of these two sequences demonstrates that over the 257 nucleotides aligned between the Brassica and Arabidopsis sequences, 172 nucleotides were identical (67% identity).

The Arabidopsis PAP sequence was also used to search proprietary databases containing corn, soybean and Arabidopsis EST sequences. Two additional Arabidopsis PAP sequences were identified, ATPAP2 (FIG. 3; SEQ ID NO: 6) and ATPAP3 (FIG. 4; SEQ ID NO: 7). Several corn ESTs and two soybean ESTs were identified, and the largest clone was obtained for further cloning and analysis. The DNA sequence of the Arabidopsis PAP corn and soybean ESTs were determined, and full length sequences were obtained using RACE-PCR. The sequence obtained for the corn PAP sequence is shown in FIG. 6 (SEQ ID NO: 9) and the two soybean PAP sequences are shown in FIGS. 7 and 8 (SEQ ID NO:10 and SEQ ID NO:11). In addition, EST sequences similar to the ATPAP1 sequence are identified from corn EST databases. The results of the search are shown in Table 1.

Corn ESTs

TABLE 1

| Seq No | Cluster ID | Clone ID | Library | NCBI gi | Method | Score | P-value | % Ident |
|---|---|---|---|---|---|---|---|---|
| 337 | 17759 | 700573361 | SATMON030 | g? | TBLASTN | 240 | 1.30E−20 | 75 |
| 338 | 17759 | 700241109 | SATMON010 | g? | TBLASTN | 254 | 5.60E−22 | 76 |
| 339 | 15287 | 700467083 | SATMON025 | g? | TBLASTN | 333 | 2.20E−30 | 75 |
| 340 | 15287 | 700467826 | SATMON025 | g? | TBLASTN | 402 | 1.10E−37 | 78 |
| 341 | 15287 | 700466226 | SATMON025 | g? | TBLASTN | 428 | 1.80E−40 | 79 |
| 342 | 5496 | 700428034 | SATMONN01 | g? | TBLASTN | 303 | 3.20E−27 | 74 |
| 343 | 5496 | 700242780 | SATMON010 | g? | TBLASTN | 359 | 4.30E−33 | 70 |
| 344 | 5496 | 700240043 | SATMON010 | g? | TBLASTN | 339 | 5.60E−31 | 67 |
| 345 | −700046467 | 700046467 | SATMON004 | g? | TBLASTN | 313 | 3.10E−28 | 63 |
| 346 | −700050949 | 700050949 | SATMON003 | g? | TBLASTN | 369 | 3.30E−34 | 73 |
| 347 | −700105029 | 700105029 | SATMON010 | g? | TBLASTN | 220 | 2.00E−18 | 72 |
| 348 | −700159470 | 700159470 | SATMON012 | g? | TBLASTN | 219 | 3.30E−18 | 61 |
| 349 | −700172426 | 700172426 | SATMON013 | g? | TBLASTN | 270 | 1.30E−23 | 62 |
| 350 | −700185072 | 700185072 | SATMON014 | g? | TBLASTN | 217 | 2.40E−25 | 76 |
| 351 | −700449914 | 700449914 | SATMON028 | g2467298 | BLASTX | 212 | 1.00E−21 | 79 |
| 352 | −700472692 | 700472692 | SATMON025 | g? | TBLASTN | 151 | 9.00E−11 | 58 |
| 353 | −700571736 | 700571736 | SATMON030 | g? | TBLASTN | 229 | 2.20E−19 | 75 |
| 354 | −700577347 | 700577347 | SATMON031 | g? | TBLASTN | 156 | 1.00E−15 | 63 |
| 355 | −700582565 | 700582565 | SATMON031 | g? | TBLASTN | 132 | 2.50E−16 | 61 |
| 356 | −700611044 | 700611044 | SATMON022 | g? | TBLASTN | 235 | 5.50E−20 | 69 |

Example 2 Yeast Expression of an Arabidopsis PAP

Constructs were prepared to express the PAP protein in yeast. The vector pCGN8521 was digested with BglII and SphI, and the PAP encoding fragment was cloned into the yeast expression vector pYES2 (Invitrogen, Carlsbad, Calif.), digested with BamHI and SphI, to yield plasmid pCGN8523.

Plasmids pCGN8523 and pYES2 were transformed into yeast strain InvSC1 (Invitrogen) using a standard lithium acetate procedure (Ausubel et al. *Current Protocols in Molecular Biology* pp13.0.1–13.13.9 (1997)). Standard yeast manipulations and media are described in Ausubel et al. (Ausubel et al. *Current Protocols in Molecular Biology* pp13.0.1–13.13.9 (1997)), and summarized here. Fifty milliliter cultures of the recombinant yeast were grown to stationary phase in SC (lacking uracil) medium with glucose. Twenty OD 600 units of cells were centrifuged and washed with SC (lacking uracil) medium with no sugar. The cells were subsequently resuspended in 100 ml of SC (lacking uracil) medium with galactose. This galactose induces expression of genes cloned under control of the gal promoter in pYES2. The yeast were grown for 2 days. Fifty milliliters of yeast cells were pelleted by centrifugation, and the lipids were extracted in 5 ml. of chloroform: methanol: 0.025 MHCl (5:10:4). Phase separation was accomplished by adding 1.2 ml of Chloroform and 1.2 ml of water. The lower chloroform phase was removed and dried under a stream of nitrogen gas. The lipid samples were resuspended in 50 ul of Hexane and loaded on a Silica TLC plate. The TLC plate was developed in Hexane:Diethyl ether:Acetic Acid (50:50:2), and the lipids were visualized by iodine staining. Two of the three lipid samples from yeast transformed with pCGN8523 showed visible diacylglycerol spots, while none of the 4 samples extracted from untransformed yeast or yeast transformed with pYES2 showed diacylglycerol spots. These data confirm that the clone Arabidopsis cDNA encodes PAP.

Example 3 Plant Expression of Arabidopsis PAP

Vectors for the expression of PAP in plants were constructed in both sense and antisense orientations. Constructs were prepared for constitutive and seed specific expression of PAP.

A plasmid containing the napin cassette derived from pCGN3223 (described in U.S. Pat. No. 5,639,790, the entirety of which is incorporated herein by reference) was modified to make it more useful for cloning large DNA fragments containing multiple restriction sites, and to allow the cloning of multiple napin fusion genes into plant binary transformation vectors. An adapter comprised of the self annealed oligonucleotide of sequence CGCGATTTAAATG-GCGCGCCCTGCAGGCGGCCGCCTG-CAGGGCGCGCCATTTAAAT (SEQ ID NO:12) was ligated into the cloning vector pBC SK+(Stratagene) after digestion with the restriction endonuclease BssHII to construct vector pCGN7765. Plamids pCGN3223 and pCGN7765 were digested with NotI and ligated together. The resultant vector, pCGN7770, contains the pCGN7765 backbone with the napin seed specific expression cassette from pCGN3223.

The cloning cassette, pCGN7787, contains essentially the same regulatory elements as pCGN7770, with the exception of the napin regulatory regions of pCGN7770 have been replaced with the double CAMV 35S promoter.

A binary vector for plant transformation, pCGN5139, was constructed using the neomycin phosphotransferase (nptII) kanamycin resistance gene driven by the CAMV 35S transcriptional initiation region (35S 5') and transcription termination (35S 3') sequences (Fraley et al., *Proc. Natl. Acad. Sci* (1983) 80:4803–4807, Gardner et al., (1986) *Plant Mol Biol* 6:221–228). The 35S 5'-nptII-35S 3' fragment was then cloned into a vector containing ori322, Right border (0.5 Kb), lacZ, Left Border (0.58 Kb), as an Xho I fragment between the Right border-lacZ and Left border sequences. The ColEI and pRi origins of replication as well as the Gentamycin resistance gene were acquired from a derivative of pCGN1532 (McBride and Summerfelt, *Plant Molecular Biology*, (1990), 14:269–276). Finally, a linker containing unique restriction sites was synthesized and cloned into the Asp 718/ Hind III (within the lacZ sequence) sites to create the binary vector pCGN5139.

3A Seed Expression Vectors

Plasmid pCGN8521 was digested with BglII and the fragment encoding PAP was cloned in the napin cassette of pCGN7770 after digestion with BglII. The resultant plasmids are pCGN8607 which contains the PAP gene in the sense orientation and pCGN8608 which contains the PAP gene in the antisense orientation. The two plasmids were digested with Asp718 and the napin/PAP gene fusions were cloned into the Asp718 digested binary vector pCGN5139. Plasmid pCGN8611 contains the napin/sense PAP gene from pCGN8607, and plasmid pCGN8612 contains the napin/antisense PAP gene from pCGN8608.

3B. Constitutive Expression Vectors

Plasmid pCGN8521 was digested with BglII and the fragment encoding PAP was cloned in the CAMV35S cassette of pCGN7787 after digestion with BamHI. The resultant plasmids were pCGN8609 which contains the PAP gene in the sense orientation and pCGN8610 which contains the PAP gene in the antisense orientation. The two plasmids were digested with Asp7l8 and the CAMV35S/PAP gene fusions were cloned into the Asp718 digested binary vector pCGN5139. Plasmid pCGN8613 contains the CAMV35S/sense PAP gene from pCGN8609, and plasmid pCGN8614 contains the CAMV35S/antisense PAP gene from pCGN8610.

Example 4 Plant Transformation

A variety of methods have been developed to insert a DNA sequence of interest into the genome of a plant host to obtain the transcription or transcription and translation of the sequence to effect phenotypic changes.

Transgenic Brassica plants are obtained by Agrobacterium-mediated transformation as described by Radke et al. (*Theor. Appl. Genet.* (1988) 75:685–694; *Plant Cell Reports* (1992) 11:499–505). Transgenic *Arabidopsis thaliana* plants may be obtained by Agrobacterium-mediated transformation as described by Valverkens et al., (*Proc. Nat. Acad. Sci.* (1988) 85:5536–5540), or as described by Bent et al. ((1994), *Science* 265:1856–1860), or Bechtold et al. ((1993), *C. R. Acad. Sci, Life Sciences* 316:1194–1199). Other plant species may be similarly transformed using related techniques.

Alternatively, microprojectile bombardment methods, such as described by Klein et al. (*Bio/Technology* 10:286–291) may also be used to obtain nuclear transformed plants.

Example 5 Transgenic Plant Analysis

Transgenic plants expressing phosphatidic acid phosphatase are analyzed using techniques known in the art. Enzyme assays are used to determine the PAP activity in leaves of control plants, plants transformed with pCGN8613, and plants transformed with pCGN8614. Leaf lipids are analyzed by thin layer chromatography to determine glycerolipid composition of the leaf lipids. Seed lipids of the control plants, plants transformed with pCGN8611, and plants transformed with pCGN8612 are analyzed for alterations in the levels of diacylglycerol, triacylglycerol, or phospholipids.

The fatty acid compositions of different lipid classes extracted from mature seeds can be examined by the following method. Analyses of the acyl compositions of the sn-2 and sn-1+3 positions of TAG are conducted using the pancreatic lipase protocol (Brockerhoff (1975), supra). Ideally with this protocol, the lipase cleaves fatty acids from the sn-1 and sn-3 positions, and not from the sn-2 position. Thus, the fatty acids in the resulting mono-glyceride are presumed to be those in the sn-2 position. However, it is noted that those previously attempting to study TAG having shorter-chain fatty acids by this method (Entressangles et al.

(1964) *Biochim. Biophys. Acta* 84:140–148), reported that shorter-chain fatty acids located at the sn-2 position were quickly hydrolyzed during such a digestion, which the authors reported to be the result of a spontaneous migration of internal shorter-chain fatty acids towards outer positions in diglycerides and monoglycerides.

Oil distilled from mature seeds may be subjected to a pancreatic lipase digestion protocol modified from Brockerhoff et al., supra, to minimize acyl migration. This distinguishes acyl compositions of the sn-2 and sn-1+3 combined positions. The modifications are as follows: pH is lowered to neutrality, reaction time is shortened from 15 to 3 minutes, samples are maintained at acidic pH thereafter, and digestion products are chromatographed on borate-impregnated TLC plants. The chromatographed products are then eluted and analyzed as fatty acid methyl esters as before.

Example 6 Isolation of PAP encoding Sequences

DNA sequences encoding PAP peptides are obtained from a PAP containing plant source of interest using synthetic oligonucleotides designed from PAP peptide sequences. The PAP nucleic acid sequences may be obtained by amplification of DNA by polymerase chain reaction (PCR) using oligonucleotides as primers, or alternatively, by screening a cDNA or genomic DNA library by radiolabeling the oligonucleotides or previously isolated sequences for use as probes.

Total RNA from the seeds of Cuphea spp and Garcinia mangifera is isolated for use in construction of a cDNA libraries. The procedure is an adaptation of the DNA isolation protocol of Webb and Knapp (D. M. Webb and S. J. Knapp, (1990) Plant Molec. Reporter, 8, 180–185). The following description assumes the use of 1 g fresh weight of tissue. Frozen seed tissue is powdered by grinding under liquid nitrogen. The powder is added to 10 ml REC buffer (50 mM Tris-HCl, pH 9, 0.8M NaCl, 10 mM EDTA, 0.5% w/v CTAB (cetyltrimethyl-ammonium bromide)) along with 0.2 g insoluble polyvinylpolypyrrolidone, and ground at room temperature. The homogenate is centrifuged for 5 minutes at 12,000×g to pellet insoluble material. The resulting supernatant fraction is filtered through Miracloth into a 3 ml phenol/chloroform preparation (phenol-saturated water/chloroform, 1/1 v/v, set to pH 7 with solid Tris base). After brief centrifugation as above to facilitate phase separation the upper phase is removed and the lower phase discarded. The upper phase is partitioned again with chloroform, and the top phase is again recovered.

The RNA is then precipitated by addition of 1 volume ethanol and collected by brief centrifugation as before. The RNA pellet is redissolved in 1 ml autoclaved 0.05% (w/v) DEPC (diethylpyrocarbonate), and reprecipitated by the addition of 1 ml 4M potassium acetate (pH 5), 0.05% (w/v) DEPC and incubation on ice for 2 hours. After collection by brief centrifugation, the RNA pellet is redissolved in 0.4 ml 0.05% (w/v) DEPC and extracted once more with phenol/chloroform as described above. Sufficient 3M potassium acetate (pH 5), 0.05% (w/v) DEPC is added to make the mixture 0.3M in acetate, followed by addition of two volumes of ethanol to precipitate the RNA. This final RNA precipitate is dissolved in 0.1 ml 0.05% (w/v) DEPC and stored frozen.

When a total RNA preparation for meadowfoam or Nausturtium spps, or other plant tissue, is desired, the Webb and Knapp protocol described above is modified as follows.

First, frozen developing seed tissue (13–20 days post pollination) from meadowfoam is used. The 10 ml REC buffer is the same as described above but with the addition of 0.1% β-mercaptoethanol. After centrifugation, the resulting supernate fraction is extracted with chloroform.

The RNA is then precipitated by addition of 1 volume RECP buffer (50 mM Tris-HCL, pH 9, 10 mM EDTA, 0.5% w/v CTAB, 0.1% β-mercaptoethanol) and collected by brief centrifugation as before. The RNA pellet is redissolved in 1 ml 0.4 m NaCL, extracted with 0.5 ml phenol/chloroform (1:1) and reprecipitated by the addition of 2 ml ethanol. After collection by brief centrifugation, the RNA pellet is dissolved in 0.4 ml $H_2O$. Optionally, 100 mg of the total RNA can be purified on an RNeasy cellulose column (Qiagen, Inc. Chatsworth, Calif.) according to the manufacturer's protocol.

Complementary DNA (cDNA) libraries are constructed from RNAs isolated above using Stratagene's (San Diego, Calif.) "UniZap" system, with the following modifications to the synthesis of first-strand cDNA. Forty micrograms of total RNA is reverse-transcribed in a 50 µl reaction volume as follows: The RNA, in $H_2O$, is heated at 65° C. for 20 minutes and chilled on ice. The first-strand synthesis is carried out as recommended by Stratagene, with the substitution of 600U "Superscript" reverse transcriptase, "Superscript" 1st-strand buffer, and DTT, all as supplied by BRL (Bethesda, Md.). The reaction mixture is incubated at 60° C. for 45 minutes. The remaining steps in the library synthesis are performed as recommended in the Stratagene "UniZap" protocol.

1. Synthetic oligonucleotide as probe: Useful hybridization solutions for library screening with oligonucleotide probes include tetraalkylammonium salt solutions, such as described by Jacobs, et al. (*Nucl. Acids Res.* (1988) 16:4637–4650). Appropriate hybridization conditions, such as hybridization and washing temperatures, may be determined by Northern analysis of RNA blots containing RNA from the enzyme source. The oligonucleotide may then be radiolabeled and hybridized with clones from the cDNA libraries described above, or from a genomic library, in order to identify clones containing sequences encoding PAP peptides.

2. PCR product as probe: PAP DNA fragments obtained by PCR may also be radiolabeled and used as probes for PAP clones (Maniatis, et al., (1989) *Molecular Cloning: A Laboratory Manual*, Second Edition, Cold Spring Harbor Laboratory, Cold Spring Harbor, N.Y.).

DNA sequences obtained are used in expression constructs for bacterial and plant transformation. Transformed plants and bacteria are analyzed for PAP expression as described above.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claim.

What is claimed is:

1. An isolated DNA sequence encoding a plant phosphatidic acid phosphatase protein, wherein said plant phosphatidic acid phosphatase protein is from *Arabidopsis thaliana*.

2. The isolated DNA sequence of claim 1, wherein said plant phosphatidic acid phosphatase protein is encoded by the sequence of SEQ ID NO: 5.

3. The isolated DNA sequence of claim 1, wherein said plant phosphatidic acid phosphatase protein is encoded by the sequence of SEQ ID NO: 6.

4. The isolated DNA sequence of claim 1, wherein said plant phosphatidic acid phosphatase protein is encoded by the sequence of SEQ ID NO: 7.

5. An isolated DNA sequence encoding a plant phosphatidic acid phosphatase protein, wherein said plant phosphatidic acid phosphatase protein is from corn.

6. The isolated DNA sequence of claim 5, wherein said plant phospbatidic acid phosphatase protein is encoded by a sequence of SEQ ID NO:9.

7. An isolated DNA sequence encoding a plant phosphatidic acid phosphatase protein, wherein said plant phosphatidic acid phosphatase protein is from soybean.

8. The isolated DNA sequence of claim 2, wherein said plant phosphatidic acid phosphatase protein is encoded by the sequence of SEQ ID NO: 10.

9. The isolated DNA sequence of claim 3, wherein said plant phosphatidic acid phosphatase protein is encoded by the sequence of SEQ ID NO:11.

10. A recombinant DNA construct comprising any one of the DNA sequences of claims 1–4, 5 and 6.

11. A recombinant DNA construct comprising, as operably linked in the 5' to 3' direction of transcription, a transcriptional initiation region functional in a plant cell, a DNA structural gene sequence encoding an *Arabidopsis thaliana* phosphatidic acid phosphatase, and a transcription termination sequence capable of terminating transcription in said plant cell.

12. A plant cell having a DNA construct comprising, as operably linked in the 5' to 3' direction of transcription, a transcriptional initiation region functional in a plant cell, a DNA structural gene sequence encoding an *Arabidopsis thaliana* phosphatidic acid phosphatase, and a transcription termination sequence capable of terminating transcription in said plant cell.

13. A plant having a plant cell comprising a DNA construct that comprises, as operably linked in the 5' to 3' direction of transcription, a transcriptional initiation region functional in a plant cell, a DNA structural gene sequence encoding an *Arabidopsis thaliana* phosphatidic acid phosphatase, and a transcription termination sequence capable of terminating transcription in said plant cell.

14. A method of modifying the lipid composition in a plant cell, said method comprising:

transforming a plant cell with DNA comprising as operably linked in the 5' to 3' direction of transcription, a transcriptional initiation region fictional in a plant cell, a DNA structural gene sequence encoding an *Arabidopsis thaliana* phosphatidic acid phosphatase, and a transcription termination sequence, capable of terminating transcription in said plant cell, and growing said plant cell under conditions wherein transcription of said *Arabidopsis thaliana* phosphatidic acid phosphatase is initiated, whereby said lipid composition is modified.

15. A method according to claim 14, wherein said encoding sequence comprises at least a portion of an *Arabidopsis thaliana* phosphatidic acid phosphatase in an antisense orientation, whereby the transcribed mRNA from said encoding sequence is complementary to the equivalent mRNA transcribed from the endogenous gene, whereby the activity of said *Arabidiopsis thaliana* phosphatidic acid phosphatase protein in said plant cell is suppressed.

16. A method according to claim 15, wherein the synthesis of triglycerides is suppressed in said plant cell.

17. A method according to claim 14, wherein said *Arabidopsis thaliana* phosphatidic acid phosphatase protein encoding sequence is in a sense orientation.

18. A method according to claim 17, wherein said lipid composition is increased.

19. A recombinant DNA construct comprising, as operably linked in the 5' to 3' direction of transcription, a transcriptional initiation region functional in a plant cell, a DNA structural gene sequence encoding a corn phosphatidic acid phosphatase, and a transcription termination sequence capable of terminating transcription in said plant cell.

20. A recombinant DNA construct comprising, as operably linked in the 5' to 3' direction of transcription, a transcriptional initiation region functional in a plant cell, a DNA structural gene sequence encoding a soybean phosphatidic acid phosphatase, and a transcription termination sequence capable of terminating transcription in said plant cell.

21. A plant cell having a DNA construct comprising, as operably linked in the 5' to 3' direction of transcription, a transcriptional initiation region functional in said plant cell, a DNA structural gene sequence encoding a corn phosphatidic acid phosphatase, and a transcription termination sequence capable of terminating transcription in said plant cell.

22. A plant cell having a DNA construct comprising, as operably linked in the 5' to 3' direction of transcription, a transcriptional initiation region functional in said plant cell, a DNA structural gene sequence encoding a soybean phosphatidic acid phosphatase, and a transcription termination sequence capable of terminating transcription in said plant cell.

23. A plant having a plant cell comprising a DNA construct that comprises, as operably linked in the 5' to 3' direction of transcription, a transcriptional initiation region functional in said plant cell, a DNA structural gene sequence encoding a corn phosphatidic acid phosphatase, and a transcription termination sequence capable of terminating transcription in said plant cell.

24. A plant having a plant cell comprising a DNA construct that comprises, as operably linked in the 5' to 3' direction of transcription, a transcriptional initiation region functional in said plant cell, a DNA structural gene sequence encoding a soybean phosphatidic acid phosphatase, and a transcription termination sequence capable of terminating transcription in said plant cell.

* * * * *

UNITED STATES PATENT AND TRADEMARK OFFICE
CERTIFICATE OF CORRECTION

PATENT NO. : 6,476,294 B1
DATED : November 5, 2002
INVENTOR(S) : Lassner et al.

It is certified that error appears in the above-identified patent and that said Letters Patent is hereby corrected as shown below:

Column 33,
Line 33, change "phospbatidic" to -- phosphatidic --;
Line 34, change "NO:9" to -- NO: 9 --;
Line 38, change "2" to -- 7 --; and
Line 40, change "3" to -- 7 --.

Column 34,
Line 19, change "fictional" to -- functional --.

Signed and Sealed this

Nineteenth Day of August, 2003

JAMES E. ROGAN
*Director of the United States Patent and Trademark Office*